US009255281B2

(12) United States Patent
Razavi-Shirazi et al.

(10) Patent No.: US 9,255,281 B2
(45) Date of Patent: *Feb. 9, 2016

(54) BIOCONVERSION PROCESSES USING WATER-INSOLUBLE LIQUIDS

(71) Applicant: Microvi Biotech, Inc., Hayward, CA (US)

(72) Inventors: Fatemeh Razavi-Shirazi, Hayward, CA (US); Mohammad Ali Dorri, Milpitas, CA (US); Ameen Razavi, Fremont, CA (US)

(73) Assignee: MICROVI BIOTECH INC., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/106,659

(22) Filed: Dec. 13, 2013

(65) Prior Publication Data

US 2014/0106420 A1    Apr. 17, 2014

Related U.S. Application Data

(63) Continuation-in-part of application No. 13/918,868, filed on Jun. 14, 2013, and a continuation-in-part of application No. PCT/US2013/046029, filed on Jun. 14, 2013.

(60) Provisional application No. 61/689,921, filed on Jun. 15, 2012, provisional application No. 61/689,922, filed on Jun. 15, 2012, provisional application No. 61/689,923, filed on Jun. 15, 2012, provisional application No. 61/689,924, filed on Jun. 15, 2012, provisional application No. 61/689,925, filed on Jun. 15, 2012, provisional application No. 61/689,929, filed on Jun. 15, 2012, provisional application No. 61/689,930, filed on Jun. 15, 2012, provisional application No. 61/689,932, filed on Jun. 15, 2012, provisional application No. 61/689,933, filed on Jun. 15, 2012, provisional application No. 61/689,935, filed on Jun. 15, 2012, provisional application No. 61/689,939, filed on Jun. 15, 2012, provisional application No. 61/689,940, filed on Jun. 15, 2012, provisional application No. 61/689,943, filed on Jun. 15, 2012, provisional application No. 61/689,945, filed on Jun. 15, 2012, provisional application No. 61/689,953, filed on Jun. 15, 2012, provisional application No. 61/849,725, filed on Feb. 1, 2013, provisional application No. 61/850,631, filed on Feb. 20, 2013, provisional application No. 61/851,467, filed on Mar. 8, 2013, provisional application No. 61/852,451, filed on Mar. 15, 2013.

(51) Int. Cl.
| | | |
|---|---|---|
| *C12P 7/06* | (2006.01) |
| *C12P 7/16* | (2006.01) |
| *C12P 7/46* | (2006.01) |
| *C12P 7/62* | (2006.01) |
| *C12N 11/04* | (2006.01) |
| *C12N 11/14* | (2006.01) |
| *C02F 3/34* | (2006.01) |
| *C12P 7/28* | (2006.01) |
| *C12P 7/56* | (2006.01) |
| *C12P 7/54* | (2006.01) |
| *C12P 7/18* | (2006.01) |
| *C12P 7/04* | (2006.01) |

(52) U.S. Cl.
CPC . *C12P 7/06* (2013.01); *C12N 11/04* (2013.01); *C12N 11/14* (2013.01); *C12P 7/04* (2013.01); *C12P 7/18* (2013.01); *C12P 7/46* (2013.01); *C12P 7/56* (2013.01); *C12P 7/62* (2013.01); *C02F 3/34* (2013.01); *C12P 7/16* (2013.01); *C12P 7/28* (2013.01); *C12P 7/54* (2013.01); *Y02E 50/17* (2013.01); *Y02W 10/37* (2015.05)

(58) Field of Classification Search
None
See application file for complete search history.

(56) References Cited

U.S. PATENT DOCUMENTS

| | | |
|---|---|---|
| 3,767,790 A | 10/1973 | Guttag |
| 4,148,689 A | 4/1979 | Hino et al. |
| 4,195,129 A | 3/1980 | Fukui et al. |
| 4,250,264 A | 2/1981 | Nelson et al. |
| 4,287,305 A | 9/1981 | Compere et al. |
| 4,352,883 A | 10/1982 | Lim |
| 4,450,233 A | 5/1984 | Mimura et al. |
| 4,469,600 A | 9/1984 | Frydman et al. |
| 4,517,298 A | 5/1985 | Tedder |
| 4,524,137 A | 6/1985 | Hagerdal et al. |

(Continued)

FOREIGN PATENT DOCUMENTS

| | | |
|---|---|---|
| EP | 0465131 A2 | 1/1992 |
| JP | 10-314782 | 12/1998 |

OTHER PUBLICATIONS

Yarris, Lynn, "New Synthetic Biology Technique Boosts Microbial Production of Diesel Fuel," Berkeley Lab, Lawrence Berkeley National Laboratory, 4 pages, Mar. 12, 2012.

(Continued)

*Primary Examiner* — John S Brusca
*Assistant Examiner* — Sharon M Papciak
(74) *Attorney, Agent, or Firm* — Dentons US LLP

(57) ABSTRACT

Processes are disclosed for bioconversion processes in which a ME biocatalyst is surrounded by water-insoluble liquid during the bioconversion to facilitate one or more of mass transfer of substrate to and bioproduct from the biocatalyst and the separation and recovery of bioproduct from the water-insoluble liquid. The ME biocatalyst irreversibly retains microorganisms for the bioconversion and has, in its interior, an aqueous environment.

14 Claims, 2 Drawing Sheets

(56) References Cited

U.S. PATENT DOCUMENTS

| | | | |
|---|---|---|---|
| 4,546,081 A | 10/1985 | Yamada et al. |
| 4,647,536 A | 3/1987 | Mosbach et al. |
| 4,659,664 A | 4/1987 | de Buda |
| 4,727,030 A | 2/1988 | Ishimura et al. |
| 4,774,178 A | 9/1988 | Egerer et al. |
| 4,791,061 A | 12/1988 | Sumino et al. |
| 4,816,399 A | 3/1989 | Lawford |
| 4,921,803 A | 5/1990 | Nohr |
| 4,950,596 A | 8/1990 | Cheng et al. |
| 4,975,375 A | 12/1990 | Haruta et al. |
| 5,034,324 A | 7/1991 | Shinozaki et al. |
| 5,071,747 A | 12/1991 | Hough et al. |
| 5,089,407 A | 2/1992 | Baker et al. |
| 5,100,673 A | 3/1992 | Bader et al. |
| 5,112,750 A | 5/1992 | Tanaka et al. |
| 5,137,818 A | 8/1992 | Harder et al. |
| 5,144,016 A | 9/1992 | Skjak-Braek et al. |
| 5,279,745 A | 1/1994 | Jeffers et al. |
| 5,290,693 A | 3/1994 | Chen et al. |
| 5,324,445 A | 6/1994 | Langley et al. |
| 5,439,859 A | 8/1995 | Durante et al. |
| 5,462,866 A | 10/1995 | Wang |
| 5,486,292 A | 1/1996 | Bair et al. |
| 5,541,234 A | 7/1996 | Unger et al. |
| 5,595,893 A | 1/1997 | Pometto, III et al. |
| 5,620,883 A | 4/1997 | Shao et al. |
| 5,840,338 A | 11/1998 | Roos et al. |
| 5,906,828 A | 5/1999 | Cima et al. |
| 6,077,432 A | 6/2000 | Coppola et al. |
| 6,133,004 A | 10/2000 | Sato et al. |
| 6,139,963 A | 10/2000 | Fujii et al. |
| 6,153,416 A | 11/2000 | Yuan |
| 6,214,619 B1 | 4/2001 | Sato et al. |
| 6,258,870 B1 | 7/2001 | Hubbell et al. |
| 6,337,019 B1 | 1/2002 | Razavi-Shirazi |
| 6,395,521 B1 | 5/2002 | Miura |
| 6,395,522 B1 | 5/2002 | DeFilippi et al. |
| 6,610,205 B2 | 8/2003 | Sato et al. |
| 6,855,513 B1 | 2/2005 | Whiteley et al. |
| 7,060,185 B2 | 6/2006 | Kim et al. |
| 7,384,777 B2 | 6/2008 | Willuweit et al. |
| 7,556,961 B2 | 7/2009 | Isaka et al. |
| 7,682,821 B2 | 3/2010 | Woods et al. |
| 7,704,733 B2 | 4/2010 | Sumino et al. |
| 7,794,590 B2 | 9/2010 | Yoshikawa et al. |
| 7,816,110 B2 | 10/2010 | Aoyama et al. |
| 7,842,185 B2 | 11/2010 | Abe et al. |
| 7,888,062 B1 | 2/2011 | Garner et al. |
| 7,923,227 B2 | 4/2011 | Hickey et al. |
| 7,931,807 B2 | 4/2011 | Bowman |
| 7,977,089 B2 | 7/2011 | Wikswo et al. |
| 8,062,873 B2 | 11/2011 | Tsai et al. |
| 8,198,055 B2 | 6/2012 | Datta et al. |
| 8,227,226 B2 | 7/2012 | Kitasaki et al. |
| 8,241,890 B2 | 8/2012 | Stloukal |
| 8,293,510 B2 | 10/2012 | Detamore et al. |
| 2002/0164364 A1 | 11/2002 | Quong |
| 2005/0037082 A1 | 2/2005 | Wan et al. |
| 2005/0269261 A1 | 12/2005 | Sublette |
| 2009/0203103 A1 | 8/2009 | Pierce et al. |
| 2009/0258404 A1 | 10/2009 | Mikkelsen et al. |
| 2010/0105116 A1 | 4/2010 | Datta et al. |
| 2010/0133114 A1 | 6/2010 | Bukshpan et al. |
| 2010/0143993 A1 | 6/2010 | Erdner-Tindall et al. |
| 2010/0230348 A1 | 9/2010 | Isaka et al. |
| 2010/0294642 A1 | 11/2010 | Datta et al. |
| 2010/0330633 A1 | 12/2010 | Walther et al. |
| 2011/0006000 A1 | 1/2011 | Post et al. |
| 2011/0053236 A1 | 3/2011 | Walmsley et al. |
| 2011/0129887 A1 | 6/2011 | Contag et al. |
| 2011/0152176 A1 | 6/2011 | Horswill |
| 2011/0183390 A1 | 7/2011 | Hickey et al. |
| 2011/0186508 A1 | 8/2011 | Bowman |
| 2011/0233125 A1 | 9/2011 | Jones et al. |
| 2012/0070888 A1 | 3/2012 | Tsai et al. |
| 2012/0115045 A1 | 5/2012 | Kapopara et al. |
| 2012/0142531 A1 | 6/2012 | Mazeaud et al. |
| 2012/0208255 A1 | 8/2012 | Andersen et al. |
| 2012/0308632 A1 | 12/2012 | Ghigo et al. |
| 2013/0022578 A1 | 1/2013 | Newman et al. |
| 2013/0023035 A1 | 1/2013 | Bielinski et al. |
| 2013/0023053 A1 | 1/2013 | March et al. |
| 2013/0034907 A1 | 2/2013 | Collins et al. |
| 2013/0035513 A1 | 2/2013 | Hu et al. |
| 2013/0109085 A1 | 5/2013 | Woods et al. |

OTHER PUBLICATIONS

Zhang et al., "Nitrate Removal by Thiobacillus Dentrificans Immobilized on Poly(vinyl alcohol) Carriers," Journal of Hazardous Materials (2008), 6 pages.

Zhou et al., "Recent Patents on Immobilized Microorganism Technology and Its Engineering Application in Wastewater Treatment," Recent Patents on Engineering, (2008), vol. 2, pp. 28-35.

Pegasus / Pegazur / Bio-Tube Process, Stowa-Selected Technologies, Jun. 13, 2006, 4 pages.

http://books.google.com/books?id_TheEtoLS8kcC &printsec=frontcover#v=onepage&q=butanol&f=false, "Handbook on Clostridia," 372, 2 pages.

http://kurakay-aqua.com.jp/en/product.pvagel.html, "PVA-Gel Bioreactor," Kuraray Aqua Co., Ltd., 3 pages.

Wu, J., et al., "Optimization of immobilization for selective oxidation of benzyl alcohol by Gluconobacter oxydans using response surface methodology," Bioresource Technology, vol. 101, 2010, pp. 8936-8941.

Seevaratnam, S., et al., "Extractive bioconversion for lactic acid production using solid sorbent and organic solvent," Bioprocess Engineering, vol. 6, 1991, pp. 35-41.

Brink, L.E.S., et al., "Automation of an Experimental System for the Microbial Epoxidation of Propene and 1-Butene," Analytica Chimica Acta, vol. 163, 1984, pp. 207-217.

Buitelaar, et al., "Application of the Liquid-Impelled Loop Reactor for the Production of Anthraquinones by Plant Cell Cultures," Current Plant Science and Biotechnology in Agriculture, vol. 9, 1990, pp. 694-699.

Bailliez, C., et al., "Growth and hydrocarbon production of Botryococcus braunii immobilized in calcium alginate gel," Appl Microbiol Biotechnol, vol. 23, 1985, pp. 99-105.

Shapiro, L., et al., "Novel alginate sponges for cell culture and transplantation," Biomaterials, vol. 18, 1997, pp. 583-590.

Smidsrod, O., et al., "Alginate as immobilization matrix for cells," Trends Biotechnol., vol. 8, Mar. 1990, pp. 71-80.

Brink, L.E.S., "Optimization of Organic Solvent in Multiphase Biocatalysis," Biotechnol Bioeng., vol. 27, Aug. 1985, pp. 1258-1269.

International Search Report and Written Opinion dated Nov. 22, 2013 corresponding to International Patent Application No. PCT/US2013/046029, 10 pages.

International Search Report and Written Opinion dated Feb. 21, 2014 corresponding to International Patent Application No. PCT/US2013/075716, 11 pages.

Barcina et al., "The Viable But Nonculturable Phenotype: A Crossroads in the Life-Cycle of Non-Differentiating Bacteria?," Rev Environ Sci Biotechnol (2009) vol. 8, pp. 245-255.

Ben-Jacob et al., "Self-Engineering Capabilities of Bacteria," J. R. Soc. Interface, (2006), vol. 3, pp. 197-214.

Chen et al., "Surface hydration: Principles and Applications Toward Low-Fouling/Nonfouling Biomaterials," Polymer 51, (2010), pp. 5283-5293.

Cho et al., "Self-Organization in High-Density Bacterial Colonies: Efficient Crowd Control," PLoS Biology, Nov. 2007, vol. 5, Issue 11, pp. 2614-2623.

Choi et al., "Engineered Materials and the Cellular Microenvironment: A Strengthening Interface Between Cell Biology and Bioengineering," Trends in Cell Biology, Dec. 2010, vol. 20, No. 12, pp. 705-714.

Christensson et al., "ANITA™ Mox-A BioFarm Solution for Fast Start-up of Deammonifying MBBRs," Sweden, WEFTEC. 2011, 18 pages.

(56) References Cited

OTHER PUBLICATIONS

Dawson et al., ""Persisters": Survival at the Cellular Level," PLoS Pathogens, Jul. 2011, vol. 7, Issue 7, pp. 1-3.
Delaittre et al., "Chemical Approaches to Synthetic Polymer Surface Biofunctionalization for Targeted Cell Adhesion Using Small Binding Motifs," Soft Matter, 2012, vol. 8, pp. 7323-7347.
Donlan, Rodney M., "Biofilms: Microbial Life on Surfaces," Emerging Infectious Diseases, vol. 8, No. 9, Sep. 2002, pp. 881-890.
Dunlop, Mary J., "Engineering Microbes for Tolerance to Next-Generation Biofuels," Dunlop Biotechnology for Biofuels, 2011, vol. 4, No. 32, pp. 1-9.
Entry et al., "Polyacrylamide Removes Microorganisms and Nutrients from Surface Water," USDA, Northwest Irrigation & Soils Research Lab, Kimberly, ID, 9 pages.
Joshi et al., "Effect of Molecular Weight on Dielectric Properties of Polyvinyl Alcohol Films," J. Appl. Polum. Sci., 102, 2006, pp. 1014-1016.
Kato et al., "Microbial Interspecies Electron Transfer via Electric Currents Through Conductive Minerals," PNAS Early Edition, pp. 1-5, 2012.
Katsikogianni et al., "Concise Review of Mechanisms of Bacterial Adhesion to Biomaterials and of Techniques Used in Estimating Bacteria-Material Interactions," Laboratory of Biomechanics and Biomedical Engineering, European Cells and Materials, vol. 8, 2004, pp. 34-57.
Kharkar et al., "Designing Degradable Hydrogels for Orthogonal Control of Cell Microenvironments," Chem. Soc. Rev., (2013), vol. 42, pp. 7335-7372.
Manina et al., "A Single-Cell Perspective on Non-Growing but Metabolically Active (NGMA) Bacteria," Current Topics in Microbiology and Immunology, (2013), 27 pages.
Mukamolova et al., "Adoption of the Transiently Non-Culturable State—a Bacterial Survival Strategy?," Advances in Microbial Physiology, (2003) vol. 47, pp. 65-129.
Nagadomi et al., "Treatment of Aquarium Water by Denitrifying Photosynthetic Bacteria Using Immobilized Polyvinyl Alcohol Beads," Journal of Bioscience and Bioengineering, vol. 87, No. 2, (1999), pp. 189-193.
Pashkuleva et al., "Surface Modification of Starch Based Biomaterials Can Simultaneously Enhance Cell Adhesion and Proliferation and Induce Bioactivity," 18th European Conference on Biomaterials, Oct. 1-4, 2003, Stuttgard, Germany, p. T103.
Quan et al., "Reject Water Treatment by Improvement of Whole Cell Anammox Entrapment Using Polyvinyl Alcohol/Alginate Gel," Biodegradation, Nov. 2011, vol. 22, Issue 6, pp. 1155-1167.
Renner et al., "Physicochemical Regulation of Biofilm Formation," MRS Bulletin, vol. 36, May 2011, pp. 1-9.
Rooke et al., "Novel Photosynthetic $CO_2$ Bioconvertor Based on Green Algae Entrapped in Low-Sodium Silica Gels," J. Mater. Chem., (2011), vol. 21, pp. 951-959.
Sousa et al., "Phenotypic Switching: An Opportunity to Bacteria Thrive," Science against microbial pathogens: communicating current research and technological advances, A. Mendez-Vilas (Ed.), FORMATEX 2011, pp. 252-262.
Stevens et al., "Exploring and Engineering the Cell Surface Interface," Science, vol. 310, Nov. 18, 2005, pp. 1135-1138.
Stolpovsky et al., "Incorporating Dormancy in Dynamic Microbial Community Models," Ecological Modeling 222(2011) pp. 3092-3102.
Sun et al., "Optimization of Entrapping Conditions of Nitrigying Bacteria and Selection of Entrapping Agent," 2nd International Conference on Environmental Science and Technology IPCBEE, vol. 6. (2011), pp. V2-414-V2-417.
Tiraferri et al., "Hydrophilic Thin-Film Composite Forward Osmosis Membranes Functionalized with Surface-Tailored Nanoparticles," ACS Appl. Materials and Interfaces (2012) vol. 4, pp. 5044-5053.
Tuson et al., "Bacteria-Surface Interactions," The Royal Society of Chemistry (2013), 13 pages.
Voloshin et al., "The Role of Intercellular Contacts in the Initiation of Growth and in the Development of a Transiently Nonculturable State by Cultures of Rhodococcus rhodochrous Grown in Poor Media," Microbiology, vol. 74, No. 4, (2005) pp. 420-427.
Wong et al., "All together now: Integrating Biofilm Research Across Disciplines," MRS Bulletin, vol. 36, May 2011, pp. 339-342.

BIOCONVERSION PROCESSES USING WATER-INSOLUBLE LIQUIDS

CROSS-REFERENCE TO RELATED APPLICATIONS

This is a continuation-in-part of U.S. patent application Ser. No. 13/918,868, filed on Jun. 14, 2013, which claims priority to U.S. Provisional Patent Applications Nos. 61/689,921, filed on Jun. 15, 2012; 61/689,922, filed on Jun. 15, 2012; 61/689,923, filed on Jun. 15, 2012; 61/689,924, filed on Jun. 15, 2012; 61/689,925, filed on Jun. 15, 2012; 61/689,929, filed on Jun. 15, 2012; 61/689,930, filed on Jun. 15, 2012; 61/689,932, filed on Jun. 15, 2012; 61/689,933, filed on Jun. 15, 2012; 61/689,935, filed on Jun. 15, 2012; 61/689,939, filed on Jun. 15, 2012; 61/689,940, filed on Jun. 15, 2012; 61/689,943, filed on Jun. 15, 2012; 61/689,945, filed on Jun. 15, 2012; 61/689,953, filed on Jun. 15, 2012; 61/849,725, filed on Feb. 1, 2013; 61/850,631, filed on Feb. 20, 2013; 61/851,467, filed on Mar. 8, 2013; and 61/852,451, filed on Mar. 15, 2013, and a continuation-in-part of International Application No. PCT/US2013/046029, designating the United States of America, filed on Jun. 14, 2013, which claims priority to U.S. Provisional Patent Applications Nos. 61/689,921, filed Jun. 15, 2012, and 61/849,725, filed on Feb. 1, 2013, all herein incorporated by reference in their entirety.

STATEMENT REGARDING FEDERALLY SPONSORED RESEARCH OR DEVELOPMENT

None

TECHNICAL FIELD

This invention pertains to bioconversion processes in which the exteriors of biocatalysts comprising microorganisms that are substantially irreversibly retained in the interior of an open, porous, highly hydrophilic polymer, are surrounded by water-insoluble liquid.

BACKGROUND

Metabolic processes have long been proposed for anabolic and catabolic bioconversions. Microorganisms of various types have been proposed for these bioconversions and include bacteria and archaea, both of which are prokaryotes; fungi; and algae. Metabolic processes are used by nature, and some have been adapted to use by man for millennia for anabolic and catabolic bioconversions ranging from culturing yogurt and fermentation of sugars to produce alcohol to treatment of water to remove contaminants. Metabolic processes offer the potential for low energy consumption, high efficiency bioconversions in relatively inexpensive processing equipment and thus may be and are often viable alternatives to chemical synthesis and degradation methods. Often anabolic processes can use raw materials that are preferred from a renewable or environmental standpoint but are not desirable for chemical synthesis, e.g., the conversion of carbon dioxide to biofuels and other bioproducts. Catabolic bioconversions can degrade substrates and have long been used for waste water treatment. Considerable interests exist in improving metabolic processes for industrial use and expanding the variety of metabolic process alternatives to chemical syntheses and degradations.

Virtually all microorganisms require the presence of water in liquid or vaporous form. Consequently, metabolic processes that have been proposed by prior workers involve the contact of an aqueous medium with the microorganisms. The aqueous medium may be a continuous phase in which the microorganisms exist or may be an aqueous phase wetting the microorganisms or support on which the microorganisms reside.

The use of an aqueous medium can pose challenges. For instance, one or more substrates or one or more metabolic products may have little, if any, solubility in water, thereby presenting mass transfer challenges. Another challenge, is the separation of the sought bioproduct from an aqueous medium. Distillation is an often used process, which can be energy intensive especially where the boiling points of the sought bioproduct and water are proximate. With some oxygenated organic compounds such as alcohols, azeotropes can form thereby presenting additional problems in the separation of the sought bioproduct from water.

Some disclosed bioprocesses inherently or by choice generate relatively dilute broths of the sought bioproduct in water. Woods, et al., in U.S. Pat. No. 7,682,821 B2, disclose a photobioreactor system in which solar energy is used to provide a concentrated ethanol product that can be more economically distilled. The patentees state that photobioreactor systems experience various limitations for use in massive scale industrial production of low-cost biofuels. One such limitation is stated to be the evaporation of ethanol from the aqueous medium. The photobioreactor comprises a chamber having a translucent or clear region to allow in sunlight to contact an aqueous fermentation medium in a lower part of the chamber wherein ethanol and water vapors can condense on the upper part of the chamber. The condensate has an enhanced ethanol concentration thus enabling more economic recovery of an anhydrous ethanol product.

In other instances, for example, fermentation processes to make butanols, including, but not limited to n-butanol and isobutanol, the butanol in the aqueous medium must be maintained relatively dilute since the butanol is toxic or inhibitory toward the microorganisms. In general, the concentration of butanol is less than about 3 volume percent in the aqueous medium. Due to the amount of water required to be removed, distillation is not the preferred recovery process. Workers have sought to modify microorganisms to increase tolerance. See, for instance, U.S. Patent Application Publication 2010/0105103 A1. Workers have also proposed extraction of butanol from the aqueous medium to maintain the butanol concentration below that which adversely affects the microorganisms. Erdner-Tindall, et al., in U.S. Patent Application Publication No. 2010/0143993 A1 have proposed processes for producing alcohols using an ionic liquid as a solvent to separate an alcohol product from a fermentation broth. They state that ionic liquids will generally have no measurable vapor pressure, have a high solubility for alcohol product, and are immiscible with the aqueous fermentation broth. They further state that the ionic liquid has little to no toxicity to the microorganism.

A prior disclosure of extraction of some bioproducts from aqueous media was made by Tedder in U.S. Pat. No. 4,517,298. The patentee discloses a process for producing simple aliphatic alcohols, most particularly ethanol, using an organic solvent containing an extractant for contact with aqueous fermentation medium withdrawn from fermentation unit. An alcohol-solvent extract phase and an aqueous phase are formed, and the alcohol is separated from the alcohol-solvent phase, e.g., by evaporation or distillation. The patentee contemplates returning the aqueous phase to the fermentation unit. The solvent system disclosed comprises a hydrophobic solvent, such as aliphatic hydrocarbon, and extractant.

Shirazi, et al., in the above-mentioned U.S. patent application Ser. No. 13/918,868 disclose biocatalysts having a high tolerance to the presence of toxins. These biocatalysts comprise i. a solid structure of hydrated hydrophilic polymer defining an interior structure having a plurality of interconnected major cavities having a smallest dimension of between about 5 to about 100 microns and an HEV of at least about 1000 and ii. a population of microorganisms capable of converting sugars to at least one organic product substantially irreversibly retained in the interior of the solid structure, said population of microorganisms being in a concentration of at least about 60 grams per liter based upon the volume defined by the exterior of the solid structure when fully hydrated wherein the microorganisms maintain their population substantially stable.

The microorganisms are believed to undergo phenotypic alterations enabling, inter alia, enhanced tolerance. The disclosed biocatalysts are particularly attractive for continuous processes for the bioconversion of fermentable sugars to ethanol as the biocatalyst is substantially devoid of solids generation, and, being a solid, enables separation of the biocatalyst from the fermentation broth. Additionally, the phenotypic alterations reduce the requirement of the microorganism for sugars for metabolic sustenance thereby enabling the bioconversion of as much as about 99 percent of the fermentable sugars to bioproducts. Moreover, the biocatalyst has a long lifetime and competition with undesired microorganism is substantially eliminated. For ease of reference, these biocatalysts are herein referred to as ME biocatalysts.

Improved processes are sought for bioconverting substrate to bioproduct where the microorganisms need to be retained in an aqueous medium.

SUMMARY

In accordance with the processes of this invention, certain biocatalyst compositions (ME biocatalysts) that substantially irreversibly retain microorganisms in their interior are surrounded by water-insoluble liquid during bioconversion of substrate to bioproduct. The ME biocatalysts exhibit enhanced tolerance, and thus the water-insoluble liquid can be chosen over a wide range of materials without undue adverse effect on the microorganisms. Hence, the water-insoluble liquid can be selected to facilitate one or more of mass transfer of substrate to and bioproduct from the biocatalyst and the separation and recovery of bioproduct from the water-insoluble liquid.

The ME biocatalysts have a high Hydration Expansion Volume (HEV) and are hydrated and thus physically protect the microorganisms from the external, water-insoluble liquid environment. The water-insoluble liquid also can, in some instances, serve to provide a hostile environment to adventitious microorganisms. The microorganisms are retained in the interior of the biocatalysts and thus are not a source of debris that can foul the biocatalyst or the water-insoluble liquid. Thus, the processes of this invention are particularly attractive for continuous metabolic operations. Further, the biocatalysts can be moved without damage to the microorganisms therein. Since the microorganisms are contained in the interior of the biocatalyst, high densities of microorganisms can be achieved in a bioreactor without operational problems such as high viscosity media that occur with high, suspended cell densities. Thus, high rates of bioconversion per unit volume of bioreactor can be achieved.

As the ME biocatalyst is surrounded by water-insoluble liquid, the processes of this invention are particularly advantageous for bioconversion processes where the substrate has little solubility in water. This preferred aspect of the invention is useful in the bioconversion of syngas and methane to oxygenated organic products. The substrate can be directly introduced into a bioreactor assembly containing the biocatalyst and water-insoluble liquid or can be contacted with the water-insoluble liquid, and a water-insoluble liquid ladened with substrate can be introduced into the bioreactor assembly for contact with the biocatalyst. The ME biocatalyst facilitates separation of the water-insoluble liquid phase and thus enables process flow design flexibility without incurring costs for, e.g., centrifugation to separate the biocatalysts.

Additionally, as the water-insoluble liquid is substantially anhydrous, bioproducts that can form azeotropes with water can typically be more readily separated from the liquid medium. The wide variety of water-insoluble liquids that are available for the practice of this invention enables the selection of a water-insoluble liquid that has appropriate properties for the separation and recovery of bioproduct. For example, where the separation is effected by distillation, the selection of the water-insoluble liquid can be based upon boiling point. In some instances, such as where the bioproduct is normally a gas, e.g., in a denitrification bioconversion, the bioproduct may pass from the water-insoluble liquid in the bioreactor assembly. In other instances, it may be desired to remove the water-insoluble liquid which contains the bioproduct from the bioreactor assembly for recovery by any suitable means, including, but not limited to, distillation, membrane separation, extraction, and crystallization.

In its broad aspect, the processes for the bioconversion of a substrate to a bioproduct comprise:

a. providing in a bioreactor assembly a water-insoluble liquid containing said substrate containing said substrate;

b. contacting said water-insoluble liquid in said bioreactor assembly with an internally hydrated biocatalyst under metabolic conditions for a time sufficient to bioconvert at least a portion of said substrate to said bioproduct wherein said water-insoluble liquid is capable of receiving said bioproduct from the interior of said biocatalyst, and in some instances, said water-insoluble liquid is a solvent for said bioproduct, to provide a bioproduct-containing liquor, said contacting being substantially absent an aqueous phase external to said biocatalyst, wherein said biocatalyst comprises:

i. a solid structure of hydrated hydrophilic polymer defining an interior structure having a plurality of interconnected major cavities having a smallest dimension of from about 5 to about 100 microns and an HEV of at least about 1000 and ii. a population of microorganisms capable of converting said substrate to said bioproduct, said population of microorganisms being substantially irreversibly retained in the interior of the solid structure, said population of microorganisms being in a concentration of at least about 60 grams per liter based upon the volume defined by the exterior of the solid structure when fully hydrated; and c. separating said bioproduct from said bioproduct-containing liquor.

The processes of this invention may be batch, semi-batch, or continuous. Often continuous processes are preferred. Especially in continuous processes, preferably at least portion of the bioproduct-containing liquor is withdrawn from the bioreactor assembly and bioproduct is separated from the withdrawn bioproduct-containing liquor to provide a regenerated liquor. The regenerated liquor may be directly passed to the bioreactor assembly, or substrate may be supplied to the least a portion of the regenerated liquor to provide a feed liquor, and the feed liquor is introduced into the bioreactor assembly as at least a portion of the water-insoluble liquid containing said substrate.

In another preferred aspect of the invention, the ME biocatalyst, which has been used for the bioconversion of substrate to bioproduct, is rehydrated. In some instances, the biocatalyst will not lose any appreciable amount of water during use. In such situations, the rehydration may serve to replenish one or more nutrients. The rehydration may occur by ceasing the contact between the biocatalyst and water-insoluble liquid, separating the biocatalyst and water-insoluble liquid and then contacting the biocatalyst with an aqueous medium for the hydration. The rehydration may occur in the bioreactor assembly, e.g., by cycling a vessel containing the biocatalyst between an external environment of the water-insoluble liquid and the aqueous medium for the hydration. Alternatively, especially in continuous processes, a portion of the biocatalyst can continuously or intermittently be withdrawn from the bioreactor assembly and any water-immiscible liquid removed therefrom. This biocatalyst can then be contacted with the aqueous medium for hydration. Preferably, the rehydration provides a biocatalyst that is fully hydrated. After hydration, the aqueous medium and biocatalyst are separated, and the rehydrated biocatalyst can be reintroduced into the bioreactor assembly. The aqueous medium for hydration of the biocatalyst preferably contains nutrients, including micronutrients, sufficient to maintain the microorganism population in the biocatalyst. Since the aqueous medium, including the nutrients, are within the interior of the ME biocatalyst and the exterior of the biocatalyst is surrounded with the water-immiscible liquid, environment can be maintained for extended periods of time in the interior of the biocatalyst that supports the microorganism population.

DETAILED DESCRIPTION

Figure 1:
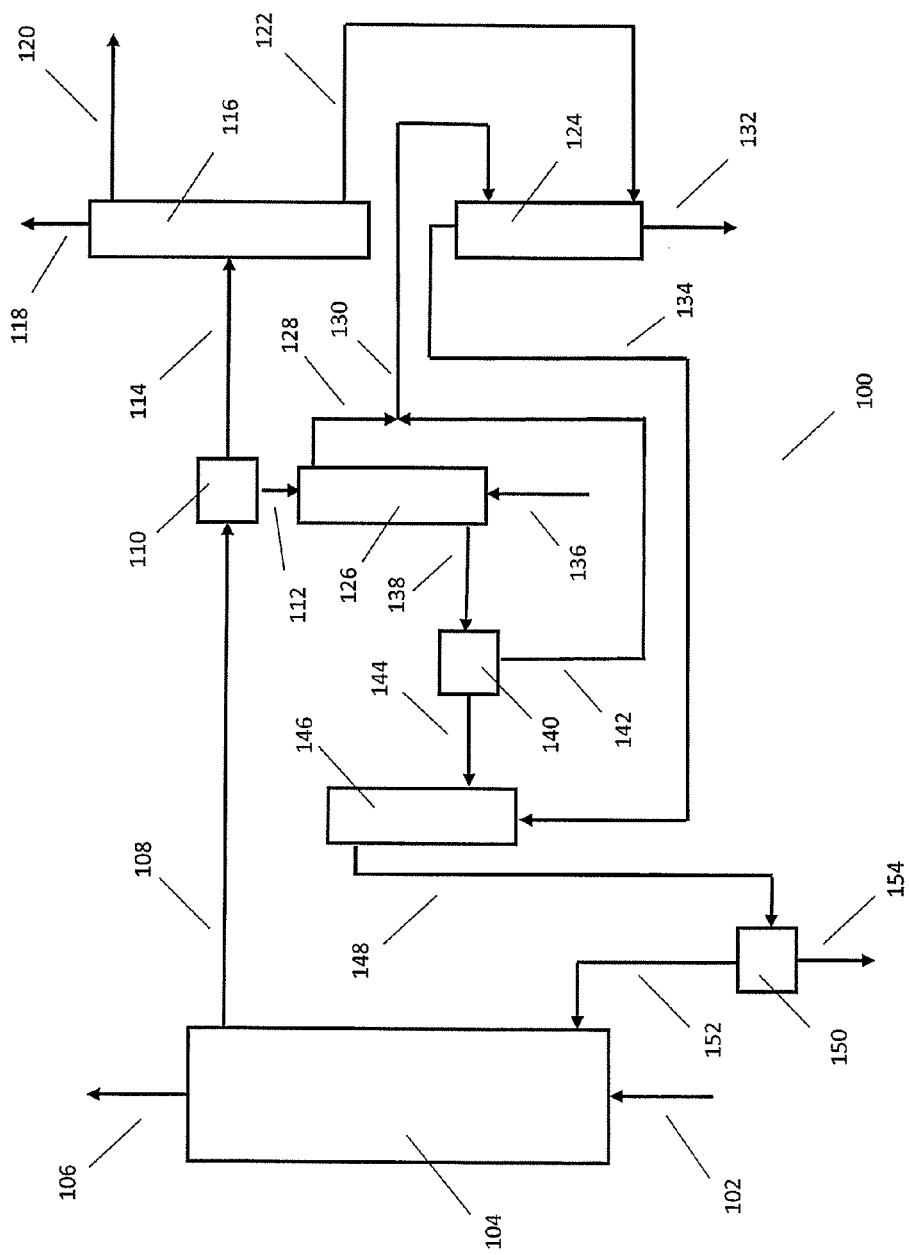
FIG. 1 is a schematic depiction of an apparatus that can be used in the processes of this invention in which a gaseous substrate is passed into a bioreactor assembly in which it is converted to an anabolic bioproduct.

All patents, published patent applications and articles referenced herein are hereby incorporated by reference in their entirety.

DEFINITIONS

As used herein, the following terms have the meanings set forth below unless otherwise stated or clear from the context of their use.

The use of the terms "a" and "an" is intended to include one or more of the element described. Lists of exemplary elements are intended to include combinations of one or more of the element described. The term "may" as used herein means that the use of the element is optional and is not intended to provide any implication regarding operability.

As used herein, the term "normally gaseous component" means the component is a gas under normal conditions of 0° C. and 101 kPa absolute.

Adhering to the solid structure of the biocatalyst means that the microorganism is located in cavities in the interior of the biocatalyst and is substantially irreversibly retained therein although extraordinary conditions and treatments (i.e., not normal bioconversion conditions for bioconversion using the microorganism) might be able in some instances to cause the microorganism to exit the biocatalyst. Adhering includes surface attachment to the polymer forming the walls of the porous matrices as well as where the microorganism are retained microorganisms that are proximate to a polymeric surface, e.g., within about 10 or about 20 microns, but not directly contacting the surface. Adhering thus includes physical and electrostatic adherence. In some instances, the polymer used to make the biocatalyst may become embedded in the extracellular polymeric substance around a cell or even in or on the cell wall of the microorganism.

Bioconversion activity is the rate of consumption of substrate per hour per gram of microorganism. Where an increase or decrease in bioconversion activity is referenced herein, such increase or decrease is ascertained under similar bioconversion conditions including concentration of substrate and product in the aqueous medium. Bioconversion activity to bioproduct is the rate of production of the bioproduct per hour per gram of microorganism.

Biofilm means an aggregate of microorganisms embedded within an extracellular polymeric substance (EPS) generally composed of polysaccharides, and may contain other components such as one or more of proteins, extracellular DNA and the polymer used to make the biocatalyst. The thickness of a biofilm is determined by the size of the aggregate contained within a continuous EPS structure, but a continuous EPS structure does not include fibrils that may extend between separated biofilms. In some instances, the biofilm extends in a random, three dimensional manner, and the thickness is determined as the maximum, straight line distance between the distal ends. A thin biofilm is a biofilm which does not exceed about 10 microns in any given direction.

Bioproduct means a product of a bioconversion which may be an anabolic product or a catabolic product and includes, but is not limited to, primary and secondary metabolites. Bioproducts include, but are not limited to, sought metabolites, co-products, and by-products, and the metabolites may be final products or intermediate products or a product which has no utility.

A bioreactor assembly is an assembly of one or more vessels suitable to contain water-insoluble liquid and ME biocatalyst and can contain associated equipment such as injectors, recycle loops, agitators, and the like.

Capable of receiving bioproduct from a biocatalyst means the bioproduct is able to pass from the interior of the biocatalyst to the water-insoluble liquid. The bioproduct may or may not dissolve in the water-insoluble liquid. For instance, a bioproduct may pass into the water-insoluble liquid as a separate phase, which may be gaseous, liquid or solid. Preferably, the bioproduct is at least partially soluble in the water-insoluble liquid.

An exo-network is a community of spaced-apart microorganisms that can be in the form of individual cells or biofilms that are interconnected by extracellular polymeric substance in the form of strands. The spacing between the microorganisms or biofilms in the exo-network is sufficient to enable the passage of nutrients and substrates there between and is often at least about 0.25, say, at least about 0.5, micron and may be as large as about 5 or about 10 microns or more.

Exterior skin is an exterior layer of polymer on the biocatalyst that is less open than the major channels in the interior structure of the biocatalyst. A biocatalyst may or may not have a skin. Where a skin is present, it may or may not have surface pores. Where no surface pores are present, fluids diffuse through the skin. Where pores are present, they often have an average diameter of between about 1 to about 10 microns.

Free liquid phase on the surface of a biocatalyst means the presence of liquid beyond that required for incipient wetness, or filling the pores or capillaries. Often the presence of free liquid results on the surface results in a glistening appearance whereas the absence of free liquid on the surface results in a dull appearance.

Fully hydrated means that a biocatalyst is immersed in water at about 25° C. until no further expansion of the superficial volume of the biocatalyst is perceived.

The "Hydration Expansion Volume" (HEV) for a biocatalyst is determined by hydrating the biocatalyst in water at about 25° C. until the volume of the biocatalyst has stabilized and measuring the superficial volume of the biocatalyst ($V_w$), removing the biocatalyst from water and removing excess water from the exterior, but without drying, and immersing the biocatalyst in ethanol at about 25° C. for a time sufficient that the volume of the biocatalyst has stabilized and then measuring the superficial volume of the biocatalyst ($V_s$).

The HEV in volume percent is calculated as the amount of $[V_w/V_s] \times 100\%$. To assure dehydration with the ethanol, either a large volume ratio of ethanol to biocatalyst is used or successive immersions of the biocatalyst in fresh ethanol are used. The ethanol is initially anhydrous ethanol.

Irreversibly retained and substantially irreversibly retained mean that the microorganism is adhering to polymeric structures defining open, porous cavities. Irreversibly retained microorganism does not include microorganisms located on the exterior surface of a biocatalyst. Microorganism is irreversibly retained even if the biocatalyst has exterior pores of sufficient size to permit egress of the microorganism.

Highly hydrophilic polymers are polymers to which water is attracted, i.e., are hydroscopic. Often the polymers exhibit, when cast as a film, a water contact angle of less than about 60°, and sometimes less than about 45°, and in some instances less than about 10°, as measured by the sessile drop method using a 5 microliter drop of pure distilled water.

Highly hydrated means that the volume of the biocatalyst (excluding the volume of the microorganisms) is at least about 90 percent water.

A matrix is an open, porous, polymeric structure and is an article of manufacture having an interconnected plurality of channels or cavities (herein "major cavities") defined by polymeric structures, said cavities being between about 5 to about 100 microns in the smallest dimension (excluding any microorganisms contained therein) wherein fluid can enter and exit the major cavities from and to the exterior of the matrix. The porous matrix may contain larger and smaller channels or cavities than the major cavities, and may contain channels and cavities not open to the exterior of the matrix. The major cavities, that is, open, interconnected regions of between about 5 or about 10 to about 70 or about 100 microns in the smallest dimension (excluding any microorganism contained therein), have nominal major dimensions of less than about 300, preferably less than about 200, microns, and sometimes a smallest dimension of at least about 10 microns. The term open, porous thus refers to the existence of channels or cavities that are interconnected by openings therebetween.

Metabolic conditions include conditions of temperature, pressure, oxygenation, pH, and nutrients (including micronutrients) and additives required or desired for the microorganisms in the biocatalyst. Nutrients and additives include growth promoters, buffers, antibiotics, vitamins, minerals, nitrogen sources, and sulfur sources and carbon sources where not otherwise provided.

Oxygenated organic product means a product containing one or more oxygenated organic compounds having 2 to 100, and frequently 2 to 50, carbons and at least one moiety selected from the group consisting of hydroxyl, carbonyl, ether and carboxyl.

Permeable means that a component can enter or exit the major cavities from or to the exterior of the biocatalyst.

Quiescent means that the aqueous medium in a biocatalyst is still; however, flows of nutrients and substrates and bioproducts can occur through the aqueous medium via diffusion and capillary flow.

Population of microorganisms refers to the number of microorganisms in a given volume and includes substantially pure cultures and mixed cultures.

A phenotypic change or alternation or phenotypic shift is a change in a microorganism's traits or characteristics from environmental factors and is thus different from a change in the genetic make-up of the microorganism.

Retained solids means that solids are retained in the interior of the biocatalyst. The solids may be retained by any suitable mechanism including, but not limited to, restrained by not being able to pass through pores in the skin of a biocatalyst, by being captured in a biofilm or a polysaccharide structure formed by microorganisms, by being retained in the polymeric structure of the biocatalyst, or by being sterically entangled within the structure of the biocatalyst or the microorganisms.

Smallest dimension means the maximum dimension of the shortest of the maximum dimensions defining the length, width and height of a major cavity. Usually a preponderance of the major cavities in a matrix are substantially width and height symmetrical. Hence the smallest dimension can be approximated by the maximum width of a cavity observed in a two dimensional cross section, e.g., by optical or electronic microscopy.

A solubilized precursor for the polymer is a monomer or prepolymer or the polymer itself that is dissolved or dispersed such that solids cannot be seen by the naked eye and is stable. For instance, a solid can be highly hydrated and be suspended in an aqueous medium even though the solid is not dissolved.

Sorption means any physical or chemical attraction and can be adsorption or absorption and may be relatively weak, e.g., about 10 kilojoules per mole or a chemical interaction with a sorbent. Preferably the sorptive attraction by the sorbent is greater than that between water and the substrate, but not so great that undue energy is required to desorb the substrate. Frequently the sorptive strength is between about 10 to about 70, say, about 15 and about 60, kilojoules per mole. A sorbent is a solid having sorptive capacity for at least one substrate.

A stable population of microorganisms means that the population of microorganisms does not decrease by more than about 50 percent nor increase by more than about 400 percent.

Substrates are carbon sources, electron donors, electron acceptors and other chemicals that can be metabolized by a microorganism, which chemicals, may or may not provide sustaining value to the microorganisms.

Sugar means carbohydrates having 5 to 12 carbon atoms and includes, but is not limited to, D-glyceraldehyde, L-glyceraldehyde, D-erythrose, L-erythrose, D-threose, L-threose, D-ribose, L-ribose, D-lyxose, L-lyxose, D-allose, L-allose, D-altrose, L-altrose 2-keto-3-deoxy D-gluconate (KDG), D-mannitol, guluronate, mannuronate, mannitol, lyxose, xylitol, D-glucose, L-glucose, D-mannose, L-mannose, D-idose, L-idose, D-galactose, L-galactose, D-xylose, L-xylose, D-arabinose, L-arabinose, D-talose, L-talose, glucuronate, galacturonate, rhamnose, fructooligosaccharide (FOS), galactooligosaccharide (GOS), inulin, mannan oligosaccharide (MOS), oligoalginate, mannuronate, guluronate, alpha-keto acid, or 4-deoxy-L-erythro-hexoselulose uronate (DEHU).

Typical Bioreactor Systems are those operated on a continuous, semi-continuous or batch mode of operation and include bioreactor assemblies such as, but are not limited to, ponds (in the case of photosynthetic processes), bubble column reactors, stirred reactors, packed bed reactors, trickle bed reactors, fluidized bed reactors, plug flow (tubular) reactors, and membrane (biofilm) reactors. In conducting photosynthetic bioconversions, the reactors may be designed to permit the transfer of photo energy. The biocatalyst may be freely mobile in the water-insoluble liquid or fixed, e.g., to a structure in the reactor vessel, or may itself provide a fixed structure. More than one reactor vessel may be used in a bioreactor assembly. For instance, reactor vessels may be in parallel or in sequential flow series.

Typical Mesophilic Conditions are metabolic conditions that include a temperature in the range of between about 0° C. to about 50° C. or more depending upon the temperature tolerance of the microorganism, most frequently, about 5° C. or about 10° C. to about 40° C. or about 45° C.; a pressure in the ranges from about 70 to about 500, say, about 90 to about 300, kPa absolute due to equipment configurations although higher and lower pressures could find applicability; and a pH in the range of between about 3 and about 9. The Typical Mesophilic Conditions can be aerobic or anaerobic.

Typical Separation Techniques for chemical products include phase separation for gaseous chemical products, the use of a still, a distillation column, liquid/liquid phase separation, gas stripping, flow-through centrifuge, Karr column for liquid-liquid extraction, mixer-settler, or expanded bed adsorption. Separation and purification steps may proceed by any of a number of approaches combining various methodologies, which may include centrifugation, filtration, reduced pressure evaporation, liquid/liquid phase separation, membranes, distillation, and/or other methodologies recited in this patent application. Principles and details of standard separation and purification steps are known in the art, for example in "Bioseparations Science and Engineering," Roger G. Harrison et al., Oxford University Press (2003), and Membrane Separations in the Recovery of Biofuels and Biochemicals—An Update Review, Stephen A. Leeper, pp. 99-194, in Separation and Purification Technology, Norman N. Li and Joseph M. Calo, Eds., Marcel Dekker (1992).

A water-insoluble liquid comprises one or more components, and water is substantially insoluble in the liquid, often less than about 0.2, preferably less than about 0.05, volume percent water is soluble in the water-insoluble liquid at about 25° C. The water-insoluble liquid is also substantially insoluble in water, often less than about 0.2, preferably less than about 0.05, volume percent of the water-insoluble liquid is soluble in water at about 25° C.

The wet weight or wet mass of cells is the mass of cells from which free water has been removed, i.e., are at the point of incipient wetness. All references to mass of cells are calculated on the basis of the wet mass of the cells.

References to organic acids herein shall be deemed to include corresponding salts and esters.

References to biocatalyst dimensions and volumes herein are of fully hydrated biocatalyst unless otherwise stated or clear from the context.

Process Discussion

This invention can be used for a wide range of anabolic and catabolic bioconversion processes. Substrates may be one or more of normally a gas, liquid or solid. The substrates preferably are capable of being dissolved in the water-insoluble liquid for contact with the ME biocatalyst although the processes can find advantageous application where the substrate has little, if any, solubility in the water-insoluble liquid but can be transported by the liquid to the biocatalysts, e.g., as a dispersion. The bioproduct is soluble in the water-insoluble liquid to facilitate its removal from the ME biocatalyst.

The substrate can be introduced into the water-insoluble liquid by any suitable technique. For instance, the substrate can be directly introduced into the bioreactor assembly. Alternatively, the substrate may first be admixed with water-insoluble liquid to form a solution, aerosol or colloidal mixture and then introduced into the bioreactor assembly. In some embodiments, the water-insoluble liquid may contact a gas or liquid containing substrate to selectively remove substrate. Any suitable apparatus may be used for the contacting, including but not limited to, scrubbers, spray towers, and liquid-liquid extraction columns. Where the water-immiscible liquid is admixed with the substrate prior to introduction into the bioreactor assembly, it is possible to effect the mixing under conditions different than those in the bioreactor assembly since microorganisms are not present. Thus, conditions of temperature and pressure can be used that facilitate the mixing and, where substrate is removed from a gas or liquid, facilitate the removal.

Substrates can be natural or xenobiotic substances in an organism (plant or animal) or can be obtained from other sources. Hence, substrates include, but are not limited to, those that can be, or can be derived from, plant, animal or fossil fuel sources, or can be produced by a chemical or industrial process. The processes of this invention can also be applicable to water supply or waste water clean-up operations where the substrate is one or more contaminants. The biocatalysts generate metabolites as a result of anabolic or catabolic activity and the metabolites may be primary or secondary metabolites. The processes of this invention can be used to produce any type of anabolic or catabolic metabolite.

Examples of substrate that may be contained in a gas phase include, but are not limited to, hydrogen, carbon monoxide, carbon dioxide, nitrogen oxides, ammonia, hydrogen sulfide, sulfur oxides, carbon disulfide, phosphine, carbonyls (such as phosgene and carbonyl sulfide), halocarbons (such as carbon tetrachloride and tetrafluoromethane), sulfur compounds (such as mercaptans and thioethers), volatile organic compounds (such as lower alkanes, lower alkenes, lower alkynes, aromatic organic compounds, alkanols, phenols, tetrahydrofurans, aldehydes, ketones, ethers, epoxides and halo-containing organic compounds.

Substrates such as sugars and oligosaccharides can find application in the processes of this invention where dispersed in the water-insoluble liquid. Lipids may also find utility as substrates. Other substrates include, but are not limited to, aliphatic and aromatic molecules, often having from, e.g., about 1 to about 44 carbon atoms which may contain hetero atoms, e.g., oxygen, sulfur, phosphorus, and nitrogen, and which may be substituted, e.g., with acyl, halogen, hydroxyl, amine, amide, thiol, nitro, or phosphine groups.

In some instances, the gases containing substrate may also contain components that may be adverse to the microorganism. Although often the biocatalyst exhibits enhance the resistance to such toxins, it may be desired to pretreat the gases to reduce the concentration of such toxins. The pretreatment may comprise any suitable unit operation including, but not limited to, sorption, chemical reaction, membrane separation, ultrafiltration, and metabolic treatment.

In some instances, the two or more substrates present may be able to be bioconverted by a single species of microorganism contained in the biocatalyst. For example, microorganisms have been proposed that are capable of converting hydrogen and carbon dioxide to ethanol as well as converting carbon monoxide to ethanol. In a bioreactor assembly more than one type of microorganism can be used, say, by using different biocatalysts, each retaining a different microorganism, or by including more than one microorganism in a biocatalyst. The different microorganisms may be used to metabolize different substrates or one may bioconvert the bioproduct of one microorganism to a further bioproduct.

Bioproducts may be degradation products especially where contaminants are being removed from a fluid such as for water supply or waste water treatment. Such degradation bioproducts include, but are not limited to, carbon dioxide, carbon monoxide, hydrogen, carbonyl sulfide, hydrogen sulfide, water, and salts such as carbonate, bicarbonate, sulfide, sulfite, sulfate, phosphate, phosphite, chloride, bromide, iodide, and borate salts of ammonium, or group 1 to 16 (IUPAC) metals such as sodium, potassium, manganese, magnesium, calcium, barium, iron, copper, cobalt, tin, selenium, radium, uranium, bismuth, cadmium, mercury, molybdenum and tungsten.

Bioproducts may be one or more of aliphatic compounds and aromatic compounds including but not limited to hydrocarbons of up to about 44 or about 50 carbons, and hydrocarbons substituted with one or more of hydroxyl, acyl, carboxyl, amine, amide, halo, nitro, sulfonyl, and phosphino moieties, and hydrocarbons containing one or more hetero atoms including but not limited to, nitrogen, sulfur, oxygen, and phosphorus atoms. Examples of organic products as end products from metabolic processes are those listed in United States published patent application no. 2010/0279354 A1, especially as set forth in paragraphs 0129 through 0149. See also, United States published patent application no. 2011/0165639 A1. Other bioproducts include p-toluate, terephthalate, terephthalic acid, aniline, putrescine, cyclohexanone, adipate, hexamethylenediamine (HMDA), 6-aminocaproic acid, malate, acrylate, apidipic acid, methacrylic acid, 3-hydroxypropionic acid (3HP), succinate, butadiene, propylene, caprolactam, fatty alcohols, fatty acids, glycerates, acrylic acid, acrylate esters, methacrylic acid, methacrylic acids, fucoidan, muconate, iodine, chlorophyll, carotenoid, calcium, magnesium, iron, sodium, potassium, and phosphate. The bioproduct may be a chemical that provides a biological activity with respect to a plant or animal or human. The biological activity can be one or more of a number of different activities such as antiviral, antibiotic, depressant, stimulant, growth promoters, hormone, insulin, reproductive, attractant, repellant, biocide, and the like. Examples of antibiotics include, but are not limited to, aminoglycosides (e.g., amikacin, gentamicin, kanamycin, neomycin, netilmicin, tobramycin, paromomycin); ansamycins (e.g., geldanamycin, herbimycin); carbacephem (loracarbef); carbapenems (e.g., ertapenem, doripenem, imipenem/cilastatin, meropenem); cephalosporins (first generation, e.g., cefadroxil, cefazolin, cefalotin, cefalexin); cephalosporins (second generation, e.g., cefaclor, cefamandole, cefoxitin, cefprozil, cefuroxime); cephalosporins (third generation, e.g., cefixime, cefdinir, cefditoren, cefoperazone, cefotaxime, cefpodoxime, ceftazidime, ceftibuten, ceftizoxime, ceftriaxone); cephalosporins (fourth generation, e.g., cefepime); cephalosporins (fifth generation, e.g., ceftobiprole); glycopeptides (e.g., teicoplanin, vancomycin, telavancin); lincosamides (e.g., clindamycin, lincomycin); macrolides (e.g., azithromycin, clarithromycin, dirithromycin, erythromycin, roxithromycin, troleandomycin, telithromycin spectinomycin); monobactams (e.g., aztreonam); nitrofurans (e.g., furazolidone, nitrofurantoin); penicillins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin); penicillin combinations (e.g., amoxicillin/clavulanate, ampicillin/sulbactam, piperacillin/tazobactam, ticarcillin/clavulanate); polypeptides (e.g., bacitracin, colistin, polymyxin B); quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin); sulfonamides (e.g., mafenide; sulfonamidochrysoidine, sulfacetamide, sulfadiazine, silver sulfadiazine, sulfamethizole, sulfamethoxazole, sulfanilimide, sulfasalazine, sulfisoxazole, trimethoprim, trimethoprim-Sulfamethoxazole (Co-trimoxazole) (TMP-SMX); tetracyclines (e.g., demeclocycline, doxycycline, minocycline, oxytetracycline, tetracycline); drugs against *mycobacteria* (e.g., clofazimine, dapsone, capreomycin, cycloserine, ethambutol, ethionamide, isoniazid, pyrazinamide, rifampin, rifabutin, rifapentine, streptomycin) and others (e.g., arsphenamine, chloramphenicol, fosfomycin, fusidic acid, linezolid, metronidazole, mupirocin, platensimycin, 1 uinupristin/dalfopristin, rifaximin, thiamphenicol, tinidazole).

Preferably an anabolic bioproduct is at least one of an oxygenated organic compound and hydrocarbon of up to about 100, often up to about 50, carbon atoms. Most preferred oxygenated organic product includes methanol, ethanol, acetic acid, n-propanol, i-propanol, propionic acid, n-butanol, i-butanol, butyric acid, acetone, and methyl ethyl ketone.

Examples of anabolic or catabolic processes suitable to be practiced by the processes of this invention include, but are not limited to:

Syngas, i.e., gas containing carbon monoxide and optionally hydrogen, for conversion to oxygenated organic product and hydrocarbons. In typical prior art processes for the conversion of syngas to oxygenated organic product, a limiting factor on productivity is the mass transfer of carbon monoxide and hydrogen from the gas phase into the liquid phase of the aqueous medium. By using the processes of this invention for syngas bioconversion, mass transfer can be enhanced.

Carbon dioxide-containing gases for conversion to oxygenated organic product and hydrocarbons. The anabolic conversion may be effected by algae, cyanobacteria, or other photo activated microorganisms, e.g., to produce alcohols, biodiesel, and like. Other bioconversion processes using carbon dioxide to produce bioproducts include those to make organic acids and esters and diacids and diesters such as succinic acid and lactic acid.

Combustion gases, e.g., from the disposal of solid wastes or generation of energy, where the substrate comprises contaminants sought to be removed from the gases such as oxygenated halides, sulfoxy moieties, nitrogen oxides, heavy metal compounds and the like.

Industrial process waste gases containing, for instance, volatile organic compounds; solvents such as chlorine containing solvents, ketones, aldehydes, peroxygenates, and the like; ammonia or volatile amines; mercaptans and other sulfur containing compounds; nitrogen oxides; and the like. The industrial process waste gases may be air-based, such as exhaust from painting operations, or maybe devoid of air such as purge or waste gases. The ability to subject these substrates to catabolic degradation can often eliminate the necessity for a thermal oxidation unit operation resulting in both capital and energy savings as often natural gas or other fuel is required to maintain temperature for the thermal oxidation unit.

Natural gas (including, but not limited to, gas recovered by underground fracturing processes, i.e., frac gas) wherein the substrate for catabolic processing may be one or more of oxygenates, such as nitrogen oxides, sulfur oxides; perchlorates; sulfides, ammonia; mercaptans; and the like or wherein the substrate for anabolic processing may be methane and other light hydrocarbons.

Carbohydrate, including, but not limited to cellulose, hemicellulose, starches, and sugars for bioconversion to oxygenated organic product and hydrocarbons.

The bioconversion processes using the ME biocatalysts may be conducted in any suitable manner employing metabolic conditions sufficient for the biocatalyst to convert the substrate to the sought bioproduct. In the processes of this invention, certain metabolic conditions are defined by the surrounding water-insoluble liquid and others are defined by the environment in the interior of the ME biocatalyst. Metabolic conditions broadly include conditions of temperature, pressure, oxygenation (oxidation reduction potential (ORP)), pH, and nutrients (including micronutrients) and additives required or desired for the microorganisms. The hydration of the interior of the ME biocatalysts provides the environment for the microorganisms and thus will define conditions such as pH, oxidation reduction potential and nutrients. As the biocatalysts are surrounded by water-insoluble liquid, water is retained in the interior of the ME biocatalysts. Due to the microenvironments and phenotypic alterations associated with the ME biocatalysts, often a broader range of metabolic conditions can be effectively used, and a broader range of conditions in the interior of the ME biocatalyst tolerated than those suitable for planktonic microorganisms.

The metabolic conditions used are those suitable for the microorganisms and the bioconversion. As stated above, the useful range of metabolic conditions are typically broader than those for planktonic bioconversion systems. In general, a microorganism can fall into the categories of psychrophile (optimal growth at −10° C. to 25° C.), a mesophile (optimal growth at 20-50° C.), a thermophile (optimal growth 45° C. to 80° C.), or a hyperthermophile (optimal growth at 80° C. to 100° C.). Many microorganisms are mesophiles and Typical Mesophilic Conditions are typically preferred.

Any suitable bioreactor assembly may be used including Typical Bioreactor Systems. The bioreactor may or may not be sterilized prior to introducing the aqueous medium. Due to the use of biocatalysts containing significant populations of microorganisms, bioreactors can have a rapid start-up time.

The bioreactor assembly contains water-insoluble liquid and ME biocatalyst. The relative amounts of the liquid and biocatalyst can fall within a broad range, especially since the microorganisms are contained within the interior of the ME biocatalyst. Preferably sufficient water-insoluble liquid is present to maintain the exterior surfaces of the biocatalyst wet.

The bioconversion processes may be optimized to achieve one or more objectives. For instance, the processes may be designed to provide high conversions of substrate to bioproduct or may be designed to balance capital and energy costs against conversion to bioproduct. As the biocatalysts are highly hydrated, generally their density is close to that of water. In some instances where the metabolic processes generate a gas, the gas can accumulate in the biocatalyst to increase buoyancy. This accumulated gas can reduce the energy consumption for a fluid bed operation and can facilitate the use of other bioreactor designs such as jet loop bioreactors.

The bioproduct may be recovered from the aqueous medium in any suitable manner including the Typical Separation Techniques.

The duration of contact between the water-insoluble liquid and the ME biocatalyst in the bioreactor assembly is sufficient to achieve a sought conversion of substrate to bioproduct. Both mass transfer and biocatalytic rates are factors in determining the duration of contact.

Hydration of the ME biocatalysts may be achieved by any suitable procedure. Typically for continuous processes a portion of the ME biocatalyst is continuously or intermittently withdrawn for rehydration and supply of nutrients (including micronutrients). Where, for instance, the substrate is not a carbon source for the microorganisms, suitable carbon source is included in the nutrients. The processes can be conducted with all carbon requirements being provided in the aqueous medium and introduced during hydration or on a carbon source deficient basis where a polysaccharide is included in the ME biocatalyst. Where operating in a carbon source deficiency, the aqueous medium often provides at least about 50, frequently at least about 75, say, about 80 to less than about 100, mass percent on a carbon basis of the carbon nutrient. The ME biocatalysts often retain nutrients (including micronutrients) and thus the demand for nutrients is that less than that for planktonic microorganisms. The rehydration can also, in some instances, serve to remove from the interior of the ME biocatalyst water soluble metabolites and microorganism waste. The frequency of rehydration will depend upon, inter alia, the nature of the microorganism and bioconversion and upon the design of the ME biocatalyst.

Water for the aqueous medium for hydration may be provided from any suitable source including, but not limited to, tap water, demineralized water, distilled water, and process or waste water streams. As stated above, this aqueous medium can contain nutrients and additives such as co-metabolites, potentiators, enhancers, inducers growth promoters, buffers, antibiotics, vitamins, minerals, nitrogen sources, and sulfur sources as is known in the art. If desired, an antifoam agent may be used in the aqueous medium. In some instances, where additives are desired or required for the metabolic process, the ME biocatalysts exhibit at least equivalent bioconversion activity at a lesser concentration of such additives as compared to a planktonic, free-suspension system, all else being substantially the same.

A wide variety of water-insoluble liquids can be used in the processes of this invention. The water-insoluble liquids may comprise one component or may be a mixture of two or more components, which preferably are miscible. For instance, where a substrate or bioproduct has limited solubility in one component, another component may be provided to co-solubilize the substrate or bioproduct. The exterior of the ME biocatalyst in the bioreactor assembly during the bioconversion process is substantially anhydrous and absent a separate water phase. Often less than about 2, say, less than about 1.5, and preferably less than about 0.5, volume percent of the total liquid to the exterior of the ME biocatalyst is a separate water phase. Accordingly, preferred processes of this invention involve unit operations to remove water from substrate and from the exterior of the ME biocatalyst after hydration prior to introduction into the bioreactor assembly.

The selection of the water-insoluble liquid is generally based upon its ability to dissolve the bioproduct, its ability to solubilize the substrate, and its compatibility with the unit operations, if any, for the recovery of the bioproduct from the water-insoluble liquid. Although some water-insoluble liquids can be deleterious to the ME biocatalyst, e.g., by dissolving the polymer of the biocatalyst, the enhanced tolerance of the microorganisms retained in the ME biocatalyst enables the use of all but the most toxic substances in the water-insoluble liquids. In some instances where the separation of the bioproduct from the water-insoluble liquid is effected by evaporation or distillation, the preferred water-insoluble liquids have a normal boiling point at least about 20° C. higher or lower than that of the bioproduct.

Examples of water-insoluble liquids include, but are not limited to, aliphatic and aromatic hydrocarbons that are liquid under the conditions of the process such as alkanes and halo-substituted alkanes of about 5 to about 20 carbons, and aromatic; alkyl-substituted aromatics and halo substituted aromatic and alkyl-substituted aromatics of about 6 to about 24 carbon atoms; alkanols of about 8 to about 24 carbon atoms; organosilicon liquids such as polydimethylsiloxane; hydrophobic organophosphates and phosphonates, e.g., containing about 10 to about 30 carbon atoms; organopolysulfide liquids; and water-insoluble ionic liquids. U.S. Patent Application Publication No. 2010/0143993 discloses various ionic liquids. This patent publication states that representative examples of typical ionic liquids are described in sources such as J. Chem. Tech. Biotechnol., 68:351-356 (1997); Chem. Ind., 68:249-263 (1996); J. Phys. Condensed Matter, 5: (supp 34B):B99-B106 (1993); Chemical and Engineering News, Mar. 30, 1998, 32-37; J. Mater. Chem., 8:2627-2636 (1998); Chem. Rev., 99:2071-2084 (1999); and US Patent Application Publication 2004/0133058. The publication further states that many ionic liquids are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form the ionic liquid. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups, since groups larger than this may produce low melting solids rather than ionic liquids. Various triarylphosphines, thioethers and cyclic and non-cyclic quaternary ammonium salts may also been used for this purpose. Counterions that may be used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal-containing anions.

ME Biocatalyst

A. ME Biocatalyst Overview

The ME biocatalysts used in the processes of this invention have a polymeric structure (matrix) defining interconnected major cavities, i.e., are open, porous matrices, in which the microorganism is retained in the interior of the matrices. It is believed that the microorganisms and their communities, inter alia, regulate their population. Also, in conjunction with the sensed nature of the microenvironment in the matrices, it is believed that the microorganisms establish a spatial relationship among the members of the community.

The microorganisms that are retained in the matrices often have the ability to form an exo-network. The quiescent nature of the cavities facilitate forming and then maintaining any formed exo-network. A discernable exo-network is not believed essential to achieving phenotypic alterations in the microorganism population such as population modulation and metabolic shift. Where an exo-network develops, often strands of EPS interconnect proximate microorganisms and connect microorganisms to the surface and form the exo-network. In some instances, the microorganisms form thin biofilms and these thin biofilms are encompassed in the exo-network. The biocatalysts have a substantial absence of biofilms in their interiors that are larger than thin biofilms. Hence, any biofilms that may ultimately form in the biocatalysts are relatively thin, e.g., up to about 10, and preferably up to about 2 or about 5, microns in thickness, and stable in size. Thus, each thin biofilm is often only a few cells and is connected in an exo-network.

Communication among the microorganisms is believed to occur through emitting chemical agents, including, but not limited to, autoinducers, and communication includes communications for community behavior and for signaling. Often, the preparation of the biocatalysts used in the processes of this invention can result in a population of microorganisms being initially located in the interior of the biocatalyst that is substantially that which would exist at the steady-state level. At these densities of microorganisms in the biocatalysts, community communications are facilitated which are believed to commence during the formation of the biocatalysts, and phenotypic shifts occur to enable the metabolic retention and modulate the population of microorganisms.

Another phenotypic alteration occurring in the biocatalysts, which is believed to be a result of this communication, is a metabolic shift, i.e., the metabolic functions of the community towards reproduction are diminished and the sought bioconversion continues. The population of microorganisms in the biocatalyst may tend to have an old average age due to this shift in the metabolic activity. Older microorganisms also tend to provide a more robust and sustainable performance as compared to younger cells as the older cells have adapted to the operating conditions.

Additional benefits of this communication can be an increase in community-level strength or fitness exhibited by the community in warding off adventitious microorganisms and maintaining strain-type uniformity. In some instances, the microorganisms during use of the biocatalyst may undergo natural selection to cause the strain-type in the community to become heartier or provide another benefit for the survival of the community of microorganisms. In some instances, the communication among the microorganisms may permit the population of microorganisms to exhibit multicellularity or multicellular-like behaviors. Thus, the population of microorganisms in a biocatalyst of this invention may have microorganisms adapting to different circumstances but yet working in unison for the benefit of the community.

In some instances the porous matrix may provide modulation of the substrate and nutrients to the microorganisms to effect to optimize metabolic pathways involving substrates that are available, and these pathways may or may not be the primarily used pathways where ample substrate and other nutrients are available. Accordingly, microorganisms in the biocatalysts may exhibit enhanced bioactivity for a primarily used pathway or metabolic activity that is normally repressed.

It is also believed that the microenvironments may promote genetic exchange or horizontal gene transfer. Conjugation or bacterial mating may also be facilitated, including the transfer of plasmids and chromosomal elements. Moreover, where microorganisms lyse, strands of DNA and RNA in the microenvironments are more readily accessible to be taken up by microorganisms in these microenvironments. These phenomena can enhance the functional abilities of the microorganisms.

The biocatalysts exhibit an increased tolerance to toxins. In some instances, communications among microorganisms and the exo-network may facilitate the population establishing defenses against toxins. For instance, the biocatalysts survive the addition of toxins such as ethanol and sodium hypochlorite and the original bioconversion activity is quickly recovered thus indicating the survival of essentially the entire community.

In summary, due to the microenvironments in the ME biocatalyst, communication among the microorganisms and the phenotypic alterations undergone by the microorganisms, the biocatalysts provide a number of process-related advantages including, but not limited to,

- no solid debris being generated,
- the potential for high densities of microorganism in a bioreactor,
- stable population of microorganisms and bioactivity over extended periods of time,
- metabolic shift of microorganisms towards production rather than growth and carbon flow shift,
- ability of microorganisms to undergo essential stasis for extended durations,
- ability to quickly respond to changes in substrate rate of supply and concentration,
- attenuation of diauxie,
- enhanced control and modulation of pH and redox balances in the microenvironment of the biocatalyst,
- greater tolerance to substrate, bioproduct and contaminants,
- ability to bioconvert substrate at ultralow concentrations,
- ability to use slower growing and less robust microorganisms and increased resistance to competitiveness,
- enhanced microorganism strain purity capabilities,
- ability to be subjected to in situ antimicrobial treatment,
- ability to quickly start a bioreactor since the density of microorganism required at full operation is contained in the biocatalyst,
- ability to contact biocatalyst with gas phase substrate, and
- ease of separation of bioproduct from biocatalyst thereby facilitating continuous operations.

If desired, the ME biocatalysts may be treated to enhance the formation of the exo-network, and if desired, thin biofilms, prior to use in the metabolic process. However, performance of the porous matrices is not generally dependent upon the extent of exo-network formation, and often bioconversion activities remain relatively unchanged between the time before the microorganisms have attached to the polymeric structure and the time when extensive exo-network structures have been generated.

B. Physical Description of the Porous Matrices

The ME biocatalysts used in the processes of this invention comprise a matrix having open, porous interior structure with microorganism irreversibly retained in at least the major cavities of the matrix.

The matrices may be a self-supporting structure or may be placed on or in a preformed structure such as a film, fiber or hollow fiber, or shaped article. The preformed structure may be constructed of any suitable material including, but not limited to, metal, ceramic, polymer, glass, wood, composite material, natural fiber, stone, and carbon. Where self-supporting, the matrices are often in the form of sheets, cylinders, plural lobal structures such as trilobal extrudates, hollow fibers, or beads which may be spherical, oblong, or free-form. The matrices, whether self-supporting or placed on or in a preformed structure, preferably have a thickness or axial dimension of less than about 5, preferably less than about 2, say, between about 0.01 to about 1, centimeters.

The porous matrices may have an isotropic or, preferably, an anisotropic structure with the exterior portion of the cross section having the densest structure. The major cavities, even if an anisotropic structure exists, may be relatively uniform in size throughout the interior of the matrix or the size of the major cavities, and their frequency, may vary over the cross-section of the biocatalyst.

The ME biocatalyst has major cavities, that is, open, interconnected regions of between about 5 or about 10 to about 70 or about 100 microns in the smallest dimension (excluding any microorganisms contained therein). For the purposes of ascertaining dimensions, the dimensions of the microorganisms includes any mass in the exo-network. In many instances, the major cavities have nominal major dimensions of less than about 300, preferably less than about 200, microns, and sometimes a smallest dimension of at least about 10 microns. Often the biocatalyst contains smaller channels and cavities which are in open communication with the major cavities. Frequently the smaller channels have a maximum cross-sectional diameter of between about 0.5 to about 20, e.g., about 1 to about 5 or about 10, microns. The cumulative volume of major cavities, excluding the volume occupied by microorganisms and mass associated with the microorganisms, to the volume of the biocatalyst is generally in the range of about 40 or about 50 to about 70 or about 99, volume percent. In many instances, the major cavities constitute less than about 70 percent of the volume of the fully catalyst with the remainder constituting the smaller channels and pores. The volume fraction of the biocatalyst that constitute the major cavities can be estimated from its cross-section. The cross section may be observed via any suitable microscopic technique, e.g., scanning electron microscopy and high powered optical microscopy. The total pore volume for the matrices can be estimated from the volumetric measurement of the matrices and the amount and density of polymer, and any other solids used to make the matrices.

The ME biocatalyst is characterized by having high internal surface areas, often in excess of at least about 1 and sometimes at least about 10, square meter per gram. In some instances, the volume of water that can be held by a fully hydrated biocatalyst (excluding the volume of the microorganisms) is in the range of about 90 to about 99 or more, percent. Preferably, the biocatalyst exhibits a Hydration Expansion Volume (HEV) of at least about 1000, frequently at least about 5000, preferably at least about 20,000, and sometimes between 50,000 to about 200,000, percent.

Usually, the type of polymer selected and the void volume percent of the matrices are such that the matrices have adequate strength to enable handling, storage and use in a bioconversion process.

The porous matrices may or may not have an exterior skin. Preferably, the matrices have an exterior skin to assist in modulating the influx and efflux of components to and from the interior channels of the porous matrix. Also, since the skin is highly hydrophilic, and additional benefit is obtained as contaminating or adventitious microorganisms have difficulties in establishing a strong biofilm on the exterior of the biocatalyst. These contaminating microorganisms are often subject to removal under even low physical forces such as by the flow of fluid around the biocatalysts. Thus, the fouling of the biocatalyst can be substantially eliminated or mitigated by washing or by fluid flows during use.

Where present, the skin typically has pores of an average diameter of between about 1 and about 10, preferably about 2 to about 7, microns in average diameter. The pores may comprise about 1 to about 30, say, about 2 to about 20, percent of the external surface area. The external skin, in addition to providing a barrier to entry of adventitious microorganisms into the interior of the biocatalyst, is preferably relatively smooth to reduce the adhesion of microorganisms to the external side of the skin through physical forces such as fluid flow and contact with other solid surfaces. Often, the skin is substantially devoid of anomalies, other than pores, greater than about 2 or about 3 microns. Where a skin is present, its thickness is usually less than about 50, say, between about 1 to about 25, microns. It should be understood that the thickness of the skin can be difficult to discern where the porous matrix has an anisotropic structure with the densest structure being at the exterior of the matrix.

A high density of microorganisms can exist at steady-state operation within the ME biocatalysts. The combination of the flow channels and the high permeability of the polymeric structure defining the channels enable viable microorganism population throughout the matrix, albeit with a plurality of unique microenvironments and nano-environments. In some instances the cell density based upon the volume of the matrices is preferably at least about 100 grams per liter, preferably at least about 150 or about 200, and often between about 250 and about 750, grams per liter.

Polysaccharide-Containing ME Biocatalysts

By incorporating polysaccharide in the interior of the ME biocatalyst, the viability of the microorganism population can be maintained. Typically polysaccharides are not usable by most microorganisms. Often, the polysaccharide is provided in an amount of at least about 0.1, say, at least about 0.2 to about 100, gram per gram of cells retained in the biocatalyst, and sometimes the biocatalyst contains between about 25 and about 500 grams of polysaccharide per liter of volume of fully hydrated biocatalyst. The polysaccharide particles used in preparing the biocatalysts preferably have a major dimension of less than about 50, preferably less than about 20, often between about 0.1 to about 5, microns. The solid polysaccharide particles are preferably granular and often have an aspect ratio of minimum cross-sectional dimension to maximum cross sectional dimension of between about 1:10 to about 1:1, say about 1:2 to about 1:1.

Due to the ability of the polysaccharide to maintain the viability of the microorganisms in the biocatalyst, the storage, handling and processes for use of the biocatalyst can be facilitated. For instance, the biocatalysts can be used in bioconversion processes which are operated in a carbon deficient manner. In metabolic processes where carbon source is added to maintain the microorganisms and not used in the sought bioconversion of substrate to bioproduct, such as in the catabolysis of nitrate, nitrite, and perchlorate anions and the metabolic reduction of metalates, the polysaccharide may serve as the sole source of carbon and thereby eliminate the necessity of adding carbon source, or it may reduce the amount of carbon source added, i.e., permit carbon deficient operation. An advantage is that the bioprocesses can be operated such that the effluent has essentially no COD. The biocatalysts also have enhanced abilities to tolerate disruptions in substrate presence and be able to quickly regain bioconversion activity.

Also, the biocatalysts can be remotely manufactured and shipped to the location of use without undue deleterious effect on the bioconversion activity of the biocatalyst. The biocatalysts may be able enter a state of essential stasis for extended durations of time in the absence of supplying substrate and other nutrients to the microbial composites even where excursions in the desired storage conditions such as temperature occur. The bioactivity can be quickly regained in a bioreactor even after extended episodic occurrences of shutdown, feedstock disruption, or feedstock variability. The biocatalysts can be packaged and shipped in sealed barrels, tanks, and the like. The polysaccharide may be from any suitable source including, but not limited to, cellulosic polysaccharides or starches. Polysaccharides are carbohydrates characterized by repeating units linked together by glycosidic bonds and are substantially insoluble in water. Polysaccharides may be homopolysaccharides or heteropolysaccharides and typically have a degree of polymerization of between about 200 to about 15,000 or more, preferably from about 200 to about 5000. The preferred polysaccharides are those in which about 10, more preferably, at least about 20, percent of the repeating units are amylose (D-glucose units). Most preferably the polysaccharide has at least about 20, more preferably, at least about 30, percent of the repeating units being amylose. The polysaccharides may or may not be functionalized, e.g., with acetate, sulfate, phosphate, pyruvyl cyclic acetal, and the like, but such functionalization should not render the polysaccharide water soluble at temperatures below about 50° C. A preferred class of polysaccharides is starches.

Sources of polysaccharides include naturally occurring and synthetic (e.g., polydextrose) polysaccharides. Various plant based materials providing polysaccharides include but are not limited to woody plant materials providing cellulose and hemicellulose, and wheat, barley, potato, sweet potato, tapioca, corn, maize, cassava, milo, rye and brans typically providing starches.

Solid Sorbent-Containing Biocatalysts

The ME biocatalysts may contain a solid sorbent. The solid sorbent may be the hydrophilic polymer forming the structure or may be a particulate, i.e., a distinct solid structure regardless of shape) contained in the solid structure. The sorbent may be any suitable solid sorbent for the substrate or nutrients or other chemical influencing the sought metabolic activity such as, but not limited to, co-metabolites, inducers, and promoters or for components that may be adverse to the microorganisms such as, and not in limitation, toxins, phages, bioproducts and by-products. The solid sorbent is typically an adsorbent where the sorption occurs on the surface of the sorbent. The particulate solid sorbents are preferably nano materials having a major dimension less than about 5 microns, preferably, between about 5 nanometers to about 3 microns. Where the solid sorbent is composed of polymer, the solid structure may be essentially entirely composed of the polymer or may be a block copolymer or polymeric mixture constituting between about 5 and about 90 mass percent of the solid structure (excluding water). Where the solid sorbent is a separate particulate in the biocatalyst, the biocatalyst may comprise between about 5 to about 90 mass percent of the mass of the biocatalyst (excluding water and microorganisms but including both the hydrophilic polymer and the particulates). More than one solid sorbent may be used in a biocatalyst. Preferably the solid sorbent is relatively uniformly dispersed throughout the interior of the biocatalyst although the solid sorbent may have a varying distribution within the biocatalyst. Where the distribution varies, the regions with the higher concentration of solid sorbent often are found toward the surface of the biocatalyst.

Where a particulate sorbent is used, the sorbent comprises an organic or inorganic material having the sought sorptive capacity. Examples of solid sorbents include, without limitation, polymeric materials, especially with polar moieties, carbon (including but not limited to activated carbon), silica (including but not limited to fumed silica), silicates, clays, molecular sieves, and the like. The molecular sieves include, but are not limited to zeolites and synthetic crystalline structures containing oxides and phosphates of one or more of silicon, aluminum, titanium, copper, cobalt, vanadium, titanium, chromium, iron, nickel, and the like. The sorptive properties may comprise one or more of physical or chemical or quasi-chemical sorption on the surface of the solid sorbent. Thus, surface area and structure may influence the sorptive properties of some solid sorbents. Frequently the solid sorbents are porous and thus provide high surface area and physical sorptive capabilities. Often the pores in the solid sorbents are in the range of about 0.3 to about 2 nanometers in effective diameter.

The solid sorbent may be incorporated into the polymeric structure in any convenient manner, preferably during the preparation of the biocatalyst.

Phosphorescent ME Biocatalysts

Another preferred aspect of the invention pertains to biocatalysts containing phosphorescent material and photosynthetic microorganisms, i.e., microorganisms that uses light energy in a metabolic process. Preferably the microorganism is an algae, most preferably a microalgae, or cyanobacteria.

The bioactivity of photosynthetic microorganisms can be enhanced to produce expressed bioproduct using broad-based light source such as sunlight. In accordance with the invention, the photosynthetic microorganisms are irreversibly retained in biocatalysts in which the interior of the biocatalyst contains phosphorescent material capable of shifting UV light to light having a wavelength of between about 400 to about 800, preferably from about 450 to about 650, nm and is capable of exhibiting persistence, with the emission of the light often lasting for at least about 5 seconds. A phosphorescent material is a material that has the ability to be excited by electromagnetic radiation into an excited state, but the stored energy is released gradually. Emissions from phosphorescent materials have persistence, that is, emissions from such materials can last for seconds, minutes or even hours after the excitation source is removed. A luminescent material is a material capable of emitting electromagnetic radiation after being excited into an excited state. Persistence is the time it takes, after discontinuing irradiation, for photoluminescent emissions emanating from a photoluminescent object to decrease to the threshold detectability.

The persistence of the radiation enables the microorganisms to be cycled in and out of a region of the culture liquid exposed to the light source and still be productive. With longer persistence durations, the photosynthetic microorganisms can continue photo-bioconversion in the absence of or reduction in light intensity. The ability of the biocatalysts to maintain photosynthetic activity over extended periods of time, often at least about 30 days, and in some instances for at least about one year, the cost of the phosphorescent materials is well offset by the increased production, reduced footprint of the bioreactor, and facilitated bioproduct recover).

The biocatalyst, being highly hydrated is a significant distributor of light radiation to photosynthetic microorganisms retained in the interior of the biocatalyst and also serves to protect the microorganism from photorespiration. The solid debris in the culture liquid (an aqueous solution comprising nutrients for metabolic processes) can be materially reduced, if not essentially eliminated, due to the microorganisms being irreversibly retained in the biocatalyst. Thus the turbidity is reduced and a given light intensity can thus be found at a greater depth in the culture liquid. These advantages provided by the ME biocatalysts can be realized in any photosynthetic process regardless of whether or not a phosphorescent material is used.

Examples of phosphorescent materials include, but are not limited to, phosphorescent materials are metal sulfide phosphors such as ZnCdS:Cu:Al, ZnCdS:Ag:Al, ZnS:Ag:Al, ZnS:Cu:Al as described in U.S. Pat. No. 3,595,804 and metal sulfides that are co-activated with rare earth elements such as those describe in U.S. Pat. No. 3,957,678. Phosphors that are higher in luminous intensity and longer in luminous persistence than the metal sulfide pigments include compositions comprising a host material that is generally an alkaline earth aluminate, or an alkaline earth silicate. The host materials generally comprise Europium as an activator and often comprise one or more co-activators such as elements of the Lanthanide series (e.g. lanthanum, cerium, praseodymium, neodymium, samarium, gadolinium, terbium, dysprosium, holmium, erbium, thulium, ytterbium, and lutetium), tin, manganese, yttrium, or bismuth. Examples of such phosphors are described in U.S. Pat. No. 5,424,006.

High emission intensity and persistence phosphorescent materials can be alkaline earth aluminate oxides having the formula $MO_m Al_2O_3:Eu^{2+}, R^{3+}$ wherein m is a number ranging from about 1.6 to about 2.2, M is an alkaline earth metal (strontium, calcium or barium), $Eu^{2+}$ is an activator, and R is one or more trivalent rare earth materials of the lanthanide series (e.g. lanthanum, cerium, praseodymium, neodymium, samarium, gadolinium, terbium, dysprosium, holmium, erbium, thulium, ytterbium, lutetium), yttrium or bismuth co-activators. Examples of such phosphors are described in U.S. Pat. No. 6,117,362. Phosphorescent materials also include alkaline earth aluminate oxides having the formula $M_k Al_2O_4:2xEu^{2+}, 2yR^{3+}$ wherein k=1-2x-2y, x is a number ranging from about 0.0001 to about 0.05, y is a number ranging from about x to 3x, M is an alkaline earth metal (strontium, calcium or barium), $Eu^{2+}$ is an activator, and R is one or more trivalent rare earth materials (e.g. lanthanum, cerium, praseodymium, neodymium, samarium, gadolinium, terbium, dysprosium, holmium, erbium, thulium, ytterbium, lutetium), yttrium or bismuth co-activators. See U.S. Pat. No. 6,267,911B1.

Phosphorescent materials also include those in which a portion of the $Al^{3+}$ in the host matrix is replaced with divalent ions such as $Mg^{2+}$ or $Zn^{2+}$ and those in which the alkaline earth metal ion ($M2^+$) is replaced with a monovalent alkali metal ion such as $Li^+$, $Na^+$, $K^+$, $Cs^+$ or $Rb^+$ such as described in U.S. Pat. Nos. 6,117,362 and 6,267,911B1.

High intensity and high persistence silicates have been disclosed in U.S. Pat. No. 5,839,718, such as Sr.BaO.Mg.MO.SiGe:Eu:Ln wherein M is beryllium, zinc or cadmium and Ln is chosen from the group consisting of the rare earth materials, the group 3A elements, scandium, titanium, vanadium, chromium, manganese, yttrium, zirconium, niobium, molybdenum, hafnium, tantalum, tungsten, indium, thallium, phosphorous, arsenic, antimony, bismuth, tin, and lead. Particularly useful are dysprosium, neodymium, thulium, tin, indium, and bismuth. X in these compounds is at least one halide atom.

Other phosphorescent materials include alkaline earth aluminates of the formula $MO.Al_2O_3.B_2O_3:R$ wherein M is a combination of more than one alkaline earth metal (strontium, calcium or barium or combinations thereof) and R is a combination of $Eu^{2+}$ activator, and at least one trivalent rare earth material co-activator, (e.g. lanthanum, cerium, praseodymium, neodymium, samarium, gadolinium, terbium, dysprosium, holmium, erbium, thulium, ytterbium, lutetium), bismuth or manganese. Examples of such phosphors can be found in U.S. Pat. No. 5,885,483. Alkaline earth aluminates of the type $MAl_2O_4$, which are described in U.S. Pat. No. 5,424,006, may also find application as may phosphorescent materials comprising a donor system and an acceptor system such as described in U.S. Pat. No. 6,953,536 B2.

As can be appreciated, many other phosphors can find application. See, for instance, Yen and Weber, Inorganic Phosphors: Compositions, Preparation and Optical Properties, CRC Press, 2004.

The phosphorescent material may be a discrete particle or may be a particle having a coating to facilitate incorporation and retention in the polymer forming the matrix. The particles may be of any suitable shape. Generally the maximum dimension of the of the particles is less than about 1 millimeter, preferably less than about 0.1 millimeter. The particles may be nanoparticles.

The persistence time exhibited by the phosphorescent materials can range from a short duration, e.g., about 5 to about 10 seconds, to as much as about 10 or about 20 hours or more and will be dependent upon the phosphorescent material used. Preferred phosphorescent materials exhibit a persistence of at least about one minute. The intensity of the emitted radiation from the polymer of the matrices will, in part, depend upon the concentration of the phosphorescent material in the polymer and the nature of the phosphorescent material. Typically the phosphorescent material is provided in an amount of at least about 0.1, say, between 0.2 and about 5 or about 10, mass percent of the polymer (non-hydrated) in the biocatalyst. One or more phosphorescent materials may be used in the biocatalyst. Where more than one phosphorescent material are used, the combination may be selected to provide one or more of wave shifting from different light wavelengths contained in the band width of the radiation source and providing differing persistence times. In preferred embodiments the phosphorescent materials are in the form of nanoparticles, e.g., having a major dimension of between about 10 nm to about 10 μm. In some instances, it may be desired to coat the phosphorescent materials with a compatibilizing agent to facilitate incorporation of the phosphorescent material within the polymer. Compatibilizing agents include, but are not limited to, molecules having one or more of hydroxyl, thiol, silyl, carboxyl, or phosphoryl groups.

C. Methods for Making ME Biocatalysts

The components, including microorganisms, used to make the ME biocatalysts and the process conditions used for the preparation of the ME biocatalysts are not critical to the broad aspects of this invention and may vary widely as is well understood in the art once understanding the principles described above. In any event, the components and process conditions for making the biocatalysts with the irreversibly, metabolically retained microorganisms should not adversely affect the microorganisms.

The ME biocatalysts may be prepared from a liquid medium containing the microorganism and solubilized precursor for the hydrophilic polymer which may be one or more of a polymerizable or solidifiable component or a solid that is fusible or bondable to form the matrix. Aqueous media are most often used due to the compatibility of most microorganisms and enzymes with water. However, with microorganisms that tolerate other liquids, such liquids can be used to make all or a portion of the liquid medium. Examples of such other liquids include, but are not limited to liquid hydrocarbons, peroxygenated liquids, liquid carboxy-containing compounds, and the like. Mixed liquid media can also be used to prepare the biocatalyst. The mixed media may comprise miscible or immiscible liquid phases. For instance, the microorganism may be suspended in a dispersed, aqueous phase and the polymerizable or solidifiable component may be contained in a continuous solvent phase.

The liquid medium used to prepare the biocatalyst may contain more than one type of microorganism, especially where the microorganisms do not significantly compete for the same substrate, and may contain one or more isolated enzymes or functional additives such as polysaccharide, solid sorbent and phosphorescent materials, as described above. Preferably, the biocatalysts contain a single type of microorganism. The concentration of the microorganisms in the liquid medium used to make the biocatalysts should at least be about 60 grams per liter. As discussed above, the concentration of microorganisms should preferably approximate the sought density of microorganisms in the biocatalyst. The relative amounts of microorganism and polymeric material in forming the biocatalyst can vary widely. The growth of the population of microorganisms post formation of the biocatalyst is contemplated as well as the potential for damage to some of the population of microorganisms during the biocatalyst-forming process. Nevertheless, higher microorganism concentrations are generally preferred, e.g., at least about 100 grams per liter, preferably at least about 200, and often between about 250 to 750, grams per liter of the liquid medium used to make the biocatalysts.

Any suitable process may be used to solidify or polymerize the polymeric material or to adhere or fuse particles to form the open, porous polymeric matrix with microorganism irreversibly retained therein. The conditions of suitable processes should not unduly adversely affect the microorganism. As microorganisms differ in tolerance to temperatures, pressures and the presence of other chemicals, some matrix-forming processes may be more advantageous for one type of microorganism than for another type of microorganism.

Preferably the polymeric matrix is formed from solidification of a high molecular weight material, by polymerization or by cross-linking of prepolymer in manner that a population of microorganisms is provided in the interior of the biocatalyst as it is being formed. Exemplary processes include solution polymerization, slurry polymerization (characterized by having two or more initial phases), and solidification by cooling or removal of solvent.

The biocatalysts may be formed in situ in the liquid medium by subjecting the medium to solidification conditions (such as cooling or evaporation) or adding a component to cause a polymerization or cross-linking or agglomeration of solids to occur to form a solid structure such as a catalyst, cross-linking agent or coagulating agent. Alternatively, the liquid medium may be extruded into a solution containing a solidification agent such as a catalyst, cross-linking or coagulating agent or coated onto a substrate and then the composite subjected to conditions to form the solid biocatalyst.

Polymeric materials used to make the biocatalysts may have an organic or inorganic backbone but have sufficient hydrophilic moieties to provide a highly hydrophilic polymer which when incorporated into the matrices exhibits sufficient water sorption properties to provide the sought Hydration Expansion Volume of the biocatalyst. Polymeric materials are also intended to include high molecular weight substances such as waxes (whether or not prepared by a polymerization process), oligomers and the like so long as they form biocatalysts that remain solid under the conditions of the bioconversion process intended for their use and have sufficient hydrophilic properties that the Hydration Expansion Volume can be achieved. As stated above, it is not essential that polymeric materials become cross-linked or further polymerized in forming the polymeric matrix.

Examples of polymeric materials include homopolymers and copolymers which may or may not be cross-linked and include condensation and addition polymers that provide high hydrophilicity and enable the Hydration Expansion Volumes to be obtained. The polymer may be a homopolymer or a copolymer, say, of a hydrophilic moiety and a more hydrophobic moiety. The molecular weight and molecular weight distribution are preferably selected to provide the combination of hydrophilicity and strength as is known in the art. The polymers may be functionalized with hydrophilic moieties to enhance hydrophilicity. Examples of hydrophilic moieties include, but are not limited to hydroxyl, alkoxyl, acyl, carboxyl, amido, and oxyanions of one or more of titanium, molybdenum, phosphorus, sulfur and nitrogen such as phosphates, phosphonates, sulfates, sulfonates, and nitrates, and the hydrophilic moieties may be further substituted with hydrophilic moieties such as hydroxyalkoxides, acetylacetonate, and the like. Typically the polymers contain carbonyl and hydroxyl groups, especially at some adjacent hydrophilic moieties such as glycol moieties. In some instances, the backbone of the polymer contains ether oxygens to enhance hydrophilicity. In some instances, the atomic ratio of oxygen to carbon in the polymer is between about 0.3:1 to about 5:1.

Polymers which may find use in forming the matrices include functionalized or non-functionalized polyacrylamides, polyvinyl alcohols, polyetherketones, polyurethanes, polycarbonates, polysulfones, polysulfides, polysilicones, olefinic polymers such as polyethylene, polypropylene, polybutadiene, rubbers, and polystyrene, nylons, polythyloxazyoline, polyethylene glycol, polysaccharides such as sodium alginate, carrageenan, agar, hyaluronic acid, chondroitin sulfate, dextran, dextran sulfate, heparin, heparin sulfate, heparin sulfate, chitosan, gellan gum, xanthan gum, guar gum, water soluble cellulose derivatives and carrageenan, and proteins such as gelatin, collagen and albumin, which may be polymers, prepolymers or oligomers, and polymers and copolymers from the following monomers, oligomers and prepolymers: monomethacrylates such as polyethylene glycol monomethacrylate, polypropylene glycol monomethacrylate, polypropylene glycol monomethacrylate, methoxydiethylene glycol methacrylate, methoxypolyethylene glycol methacrylate, methacryloyloxyethyl hydrogen phthalate, methacryloyloxyethyl hydrogen succinate, 3-chloro-2-hydroxypropyl methacrylate, stearyl methacrylate, 2-hydroxy methacrylate, and ethyl methacrylate; monoacrylates such as 2-hydroxyethyl acrylate, 2-hydroxypropyl acrylate, isobutyl acrylate, t-butyl acrylate, isooctyl acrylate, lauryl acrylate, stearyl acrylate, isobornyl acrylate, cyclohexyl acrylate, methoxytriethylene glycol acrylate, 2-ethoxyethyl acrylate, tetrahydrofurfuryl acrylate, phenoxyethyl acrylate, nonylphenoxypolyethylene glycol acrylate, nonylphenoxypolypropylene glycol acrylate, silicon-modified acrylate, polypropylene glycol monoacrylate, phenoxyethyl acrylate, phenoxydiethylene glycol acrylate, phenoxypolyethylene glycol acrylate, methoxypolyethylene glycol acrylate, acryloyloxyethyl hydrogen succinate, and lauryl acrylate; dimethacrylates such as 1,3-butylene glycol dimethacrylate, 1,4-butanediol dimethacrylate, ethylene glycol dimethacrylate, diethylene glycol dimethacrylate, triethylene glycol dimethacrylate, polyethylene glycol dimethacrylate, butylene glycol dimethacrylate, hexanediol dimethacrylate, neopentyl glycol dimethacrylate, polyprene glycol dimethacrylate, 2-hydroxy-1,3-dimethacryloxypropane, 2,2-bis-4-methacryloxyethoxyphenylpropane, 3,2-bis-4-methacryloxydiethoxyphenylpropane, and 2,2-bis-4-methacryloxypolyethoxyphenylpropane; diacrylates such as ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxyethoxyphenylpropane, 2-hydroxy-1-acryloxy-3-methacryloxypropane; trimethacrylates such as trimethylolpropane trimethacrylate; triacrylates such as trimethylolpropane triacrylate, pentaerythritol triacrylate, trimethylolpropane EO-added triacrylate, glycerol PO-added triacrylate, and ethoxylated trimethylolpropane triacrylate; tetraacrylates such as pentaerythritol tetraacrylate, ethoxylated pentaerythritol tetraacrylate, propoxylated pentaerythritol tetraacrylate, and ditrimethylolpropane tetraacrylate; urethane acrylates such as urethane acrylate, urethane dimethyl acrylate, and urethane trimethyl acrylate; amino-containing moieties such as 2-aminoethyl acrylate, 2-aminoethyl methacrylate, aminoethyl methacrylate, dimethyl aminoethyl methacrylate, monomethyl aminoethyl methacrylate, t-butylaminoethylmethacrylate, p-aminostyrene, o-aminostyrene, 2-amino-4-vinyltoluene, dimethylaminoethyl acrylate, diethylaminoethyl acrylate, piperidinoethyl ethyl acrylate, piperidinoethyl methacrylate, morpholinoethyl acrylate, morpholinoethyl methacrylate, 2-vinyl pyridine, 3-vinyl pyridine, 2-ethyl-5-vinyl pyridine, dimethylaminopropylethyl acrylate, dimethylaminopropylethyl methacrylate, 2-vinyl pyrrolidone, 3-vinyl pyrrolidone, dimethylaminoethyl vinyl ether, dimethylaminoethyl vinyl sulfide, diethylaminoethyl vinyl ether, 2-pyrrolidinoethyl acrylate, 2-pyrrolidinoethyl methacrylate, and other monomers such as acrylamide, acrylic acid, and dimethylacrylamide.

Not all the above listed polymers will be useful by themselves, but may be required to be functionalized or used to form a co-polymer with a highly hydrophilic polymer.

Cross linking agents, accelerators, polymerization catalysts, and other polymerization additives may be employed such as triethanolamine, triethylamine, ethanolamine, N-methyl diethanolamine, N,N-dimethyl benzylamine, dibenzyl amino, N-benzyl ethanolamine, N-isopropyl benzylamino, tetramethyl ethylenediamine, potassium persulfate, tetramethyl ethylenediamine, lysine, ornithine, histidine, arginine, N-vinyl pyrrolidinone, 2-vinyl pyridine, 1-vinyl imidazole, 9-vinyl carbazone, acrylic acid, and 2-allyl-2-methyl-1,3-cyclopentane dione. For polyvinyl alcohol polymers and copolymers, boric acid and phosphoric acid may be used in the preparation of polymeric matrices. As stated above, the amount of cross-linking agent may need to be limited to assure that the matrices retain high hydrophilicity and the ability to have a high Hydration Expansion Volume. The selection of the polymer and cross-linking agents and other additives to make porous matrices having the physical properties set forth above is within the level of the artisan in the art of water soluble and highly hydrophilic polymer synthesis.

The ME biocatalysts may be formed in the presence of other additives which may serve to enhance structural integrity or provide a beneficial activity for the microorganism such as attracting or sequestering components, providing nutrients, and the like. Additives can also be used to provide, for instance, a suitable density to be suspended in the aqueous medium rather than tending to float or sink in the broth. Typical additives include, but are not limited to, starch, glycogen, cellulose, lignin, chitin, collagen, keratin, clay, alumina, aluminosilicates, silica, aluminum phosphate, diatomaceous earth, carbon, polymer, polysaccharide and the like. These additives can be in the form of solids when the polymeric matrices are formed, and if so, are often in the range of about 0.01 to 100 microns in major dimension.

If desired, where the biocatalyst contains microorganisms, they may be subjected to stress as is known in the art. Stress may be one or more of starvation, chemical or physical conditions. Chemical stresses include toxins, antimicrobial agents, and inhibitory concentrations of compounds. Physical stresses include light intensity, UV light, temperature, mechanical agitation, pressure or compression, and desiccation or osmotic pressure. The stress may produce regulated biological reactions that protect the microorganisms from shock and the stress may allow the hardier microorganisms to survive while the weaker cells die.

Microorganism

The microorganism for a ME biocatalyst is one or more microorganisms. In another aspect, the biocatalysts can contain, in addition to the microorganisms, one or more extracellular enzymes, or isolated enzymes, in the interior of the biocatalyst to cause a catalytic change to a component which may be substrate or other nutrients, or a bioproduct or by-product or co-product of the microorganisms, or may be a toxin, phage or the like.

Examples of enzymes include, but are not limited to, one or more of oxidoreductases, transferases, hydrolases, lyases, isomerases, and ligases. The enzymes may cause one or more metabolic conversions. For instance, an enzyme may metabolize a component in the feed such that it can be bioconverted, or more easily be bioconverted, by the microorganisms in the biocatalyst. An enzyme may be used to metabolize a metabolite of the microorganism either to provide a sought bioproduct. An enzyme may be used to metabolize a component in the feed or a co-metabolite from the microorganism that may be adverse to the microorganism into a metabolite that is less adverse to the microorganism. If desired, two or more different enzymes can be used to effect a series of metabolic conversions on a component in the feed or a metabolite from the microorganism.

Representative enzymes include, without limitation: cellulase, cellobiohydrolase (e.g., CBHI, CBHII), alcohol dehydrogenase (A, B, and C), acetaldehyde dehydrogenase, amylase, alpha amylase, glucoamylase, beta glucanase, beta glucosidase, invertase, endoglucanase (e.g., EGI, EGII, EGIII), lactase, hemicellulase, pectinase, hydrogenase, pullulanase, phytase, a hydrolase, a lipase, polysaccharase, ligninase, Accellerase® 1000, Accellerase® 1500, Accellerase® DUET, Accellerase® TRIO, or Cellic CTec2 enzymes, phosphoglucose isomerase, inositol-1-phosphate synthase, inositol monophosphatase, myo-inositol dehydrogenase, myo-inosose-2-dehydratase, inositol 2-dehydrogenase, deoxy-D-gluconate isomerase, kinase, 5-dehydro-2-deoxygluconokinase, deoxyphophogluconate aldolase, 3-hydroxy acid dehydrogenase, isomerase, topoisomerase, dehydratase, monosaccharide dehydrogenase, aldolase, phosphatase, a protease, DNase, alginate lyase, laminarinase, endoglucanase, L-butanediol dehydrogenase, acetoin reductase, 3-hydroxyacyl-CoA dehydrogenase, or cis-aconitate decarboxylase. The enzymes include those described by Heinzelman et al. (2009) *PNAS* 106: 5610-5615, herein incorporated by reference in its entirety.

The enzymes may be bound to the precursor for the hydrophilic polymer of the biocatalyst prior to the formation of the biocatalyst or may be introduced during the preparation of the biocatalyst, e.g., by addition to the liquid medium for forming the biocatalyst. There are many methods that would be known to one of skill in the art for providing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process. Various methods are described in Methods in Enzymology, Immobilized Enzymes and Cells, Part C. 1987. Academic Press. Edited by S. P. Colowick and N. O. Kaplan. Volume 136; Immobilization of Enzymes and Cells. 1997. Humana Press. Edited by G. F. Bickerstaff. Series: Methods in Biotechnology, Edited by J. M. Walker; DiCosimo, R., McAuliffe, J., Poulose, A. J. Bohlmann, G. 2012. Industrial use of immobilized enzymes. Chem. Soc. Rev.; and Immobilized Enzymes: Methods and Applications. Wilhelm Tischer and Frank Wedekind, Topics in Current Chemistry, Vol. 200. Page 95-126.

Typically extracellular enzymes bond or adhere to solid surfaces, such as the hydrophilic polymer, solid additives, cell walls and extracellular polymeric substance. Hence, the enzymes can be substantially irreversibly retained in the interior of the biocatalyst. Due to the structure of the ME biocatalysts, the microorganisms and the enzymes can be in close proximity and thus effective, cooperative bioconversions can be obtained. The association of the enzymes with the interior surfaces of the biocatalyst typically increases the resistance of the enzyme or enzymes to denaturation due to changes in temperature, pH, or other factors related to thermal or operational stability of the enzymes. Also, by being retained in the biocatalyst, the use of the enzyme in a bioreactor is facilitated and undesirable post-reactions can be mitigated.

The microorganisms used in the ME biocatalysts may be unicellular or may be multicellular that behaves as a single cell microorganism such as filamentous growth microorganisms and budding growth microorganisms. Often the cells of multicellular microorganisms have the capability to exist singularly. The microorganisms can be of any type, including, but not limited to, those microorganisms that are aerobes, anaerobes, facultative anaerobes, heterotrophs, autotrophs, photoautotrophs, photoheterotrophs, chemoautotrophs, and/or chemoheterotrophs. The cellular activity, including cell growth can be aerobic, microaerophilic, or anaerobic. The cells can be in any phase of growth, including lag (or conduction), exponential, transition, stationary, death, dormant, vegetative, sporulating, etc. The one or more microorganisms be a psychrophile (optimal growth at about $-10°$ C. to about $25°$ C.), a mesophile (optimal growth at about 20-about $50°$ C.), a thermophile (optimal growth about $45°$ C. to about $80°$ C.), or a hyperthermophile (optimal growth at about $80°$ C. to about $100°$ C.). The one or more microorganisms can be a gram-negative or gram-positive bacterium. A bacterium can be a cocci (spherical), bacilli (rod-like), or spirilla (spiral-shaped; e.g., vibrios or comma bacteria). The microorganisms can be phenotypically and genotypically diverse.

The microorganisms can be a wild-type (naturally occurring) microorganism or a recombinant (including, but not limited to genetically engineered microorganisms) microorganism. A recombinant microorganism can comprise one or more heterologous nucleic acid sequences (e.g., genes). One or more genes can be introduced into a microorganism used in the methods, compositions, or kits described herein, e.g., by homologous recombination. One or more genes can be introduction into a microorganism with, e.g., a vector. The one or more microorganisms can comprise one or more vectors. A vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain a means for self-replication. The vector can, when introduced into a host cell, integrate into the genome of the host cell and replicate together with the one or more chromosomes into which it has been integrated. Such a vector can comprise specific sequences that can allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants. Means of genetically manipulating organisms are described, e.g., Current Protocols in Molecular Biology, last updated Jul. 25, 2011, Wiley, Print ISSN: 1934-3639. In some embodiments, one or more genes involved in byproduct formation are deleted in a microorganism. In some embodiments, one or more genes involved in byproduct formation are not deleted. Nucleic acid introduced into a microorganism can be codon-optimized for the microorganism. A gene can be modified (e.g., mutated) to increase the activity of the resulting gene product (e.g., enzyme).

The selected microorganism to be used in a biocatalyst can be targeted to the sought activity. The biocatalysts thus often contain substantially pure strain types of microorganisms and, because of the targeting, enable high bioactivity to be achieved and provide a stable population of the microorganism in the biocatalyst.

Representative microorganisms for making ME biocatalysts include, without limitation, those set forth in United States published patent application nos. 2011/0072714, especially paragraph 0122; 2010/0279354, especially paragraphs 0083 through 0089; 2010/0185017, especially paragraph 0046; 2009/0155873; especially paragraph 0093; and 2006/0063217, especially paragraphs 0030 and 0031, and those set forth in Appendix A hereto.

Photosynthetic microorganisms include bacteria, algae, and molds having biocatalytic activity activated by light radiation. Examples of photosynthetic microorganisms for higher oxygenated organic compound production include, but are not limited to alga such as Bacillariophyceae strains, Chlorophyceae, Cyanophyceae, Xanthophyceaei, Chrusophyceae, *Chlorella* (e.g., *Chlorella prototheocoides*), Crypthecodinium, Schizocytrium, Nannochloropsis, Ulkenia, Dunaliella, Cyclotella, Navicula, Nitzschia, Cyclotella, Phaeodactylum, and Thaustochytrids; yeasts such as *Rhodotorula, Saccharomyces*, and Apiotrichum strains; and fungi species such as the *Mortierella* strain. Genetically enhanced photoautotrophic cyanobacteria, algae, and other photoautotrophic organisms have been adapted to bioconvert carbohydrates internal to the microorganism directly to ethanol, butanol, pentanol and other higher alcohols and other biofuels. For example, genetically modified cyanobacteria having constructs comprising DNA fragments encoding pyruvate decarboxylase (pdc) and alcohol dehydrogenase (adh) enzymes are described in U.S. Pat. No. 6,699,696. Cyanobacteria are photosynthetic bacteria which use light, inorganic elements, water, and a carbon source, generally carbon dioxide, to metabolize and grow. The production of ethanol using genetically engineered cyanobacteria has also been described in PCT Published Patent Application WO 2007/084477.

DRAWINGS

The processes of the invention will be further described in connection with FIGS. 1 and 2. The figures omit minor equipment such as pumps, compressors, valves, instruments and other devices the placement of which and operation thereof are well known to those practiced in chemical engineering. The figures also all omit ancillary unit operations. The apparatus depicted in FIG. 2 may be used to obtain substrate from gaseous streams or liquid streams.

FIG. 1 is a schematic depiction of an apparatus generally designated as 100 suitable for practicing the processes of this invention. Feedstock containing substrate, which for purposes of discussion is carbon dioxide, is provided via line 102 to bioreactor assembly 104. As depicted bioreactor assembly 104 is a photosynthetic bioreactor provides for contact between the substrate and water-insoluble liquid, which for purposes of discussion is dodecanol. Bioreactor assembly 104 contains ME biocatalyst in the form of spheres of about 2 millimeters in diameter. The ME biocatalyst contains photosynthetic microorganism capable of bioconverting carbon dioxide to ethanol such as a cyanobacteria. As shown, the upward flow of carbon dioxide searched to agitate the ME biocatalyst in bioreactor assembly 104. Unreacted carbon dioxide exits bioreactor assembly 104 via line 106. Some ethanol contained in the water-insoluble liquid may be stripped by carbon dioxide not dissolved in the water insoluble liquid and will be contained in the carbon dioxide exiting the bioreactor assembly via line 106. The unreacted carbon dioxide in line 106 may be recycled to bioreactor assembly 104. A stream of water-insoluble liquid containing ethanol is withdrawn from bioreactor assembly 104 via line 108 and this stream contains entrained ME biocatalyst.

Line 108 directs the ME biocatalyst-containing liquid to solid separator 110 where biocatalyst is separated from the water-insoluble liquid. The separated biocatalyst is passed via line 112 to rehydration tank 126. The water-insoluble liquid is withdrawn from solid separator 110 and passes the line 114 to distillation column 116. Since the water-insoluble liquid has an essential absence of water, the distillation provides a substantially anhydrous, ethanol product which is withdrawn from distillation column 116 via line 120. Lights such as dissolved carbon dioxide exit distillation column 116 via line 118. A bottoms fraction containing dodecanol and being substantially devoid of ethanol is withdrawn via line 122.

The bottoms fraction in line 122 and is passed to liquid-liquid extraction unit 124. Extraction unit 124 serves to remove any water-soluble impurities in the dodecanol such as esters and acids. The water for the extraction unit is supplied via line 130 and countercurrent contact occurs with spent water being removed from extraction unit 124 via line 132. A raffinate, which is the water-insoluble liquid, exits extraction unit 124 via line 134.

Returning now to the ME biocatalyst passed to rehydration tank 126, line 136 supplies an aqueous medium containing replacement nutrients for the biocatalyst to rehydration tank 126 for contact with the biocatalyst. This aqueous medium is provided at a lower portion of rehydration tank 126 for countercurrent contact with the biocatalyst. The aqueous medium is withdrawn from an upper portion of rehydration tank 126 via line 128. The aqueous medium will contain some ethanol which was retained in the biocatalyst separated from the water-insoluble liquid. This aqueous medium constitutes a portion of the water used in extraction unit 124. A portion of the contained ethanol will be extracted from the aqueous phase in extraction unit 124 by the dodecanol. A slurry of biocatalyst exits rehydration tank 126 via line 138 and is passed to solids separator 140. In solids separator 140 the biocatalyst is separated from the aqueous medium. The aqueous medium exits via line 142 and is passed to line 134 use as the aqueous medium for extraction unit 124.

The biocatalyst from solid separator 140 is passed via line 144 to mixing tank 146 where it is contacted with the raffinate in line 134 obtained from extraction unit 124. A slurry of biocatalyst in the water-insoluble liquid is produced in mixing tank 146, and the slurry is passed via line 148 to knockout pot 150. Water that passes to the exterior of the biocatalyst will exist as a separate phase and will be collected in knockout pot 150 and removed via line 154. A slurry of biocatalyst in water-insoluble liquid is directed to bioreactor assembly 104 via line 152 from knockout pot 150.

Figure 2:
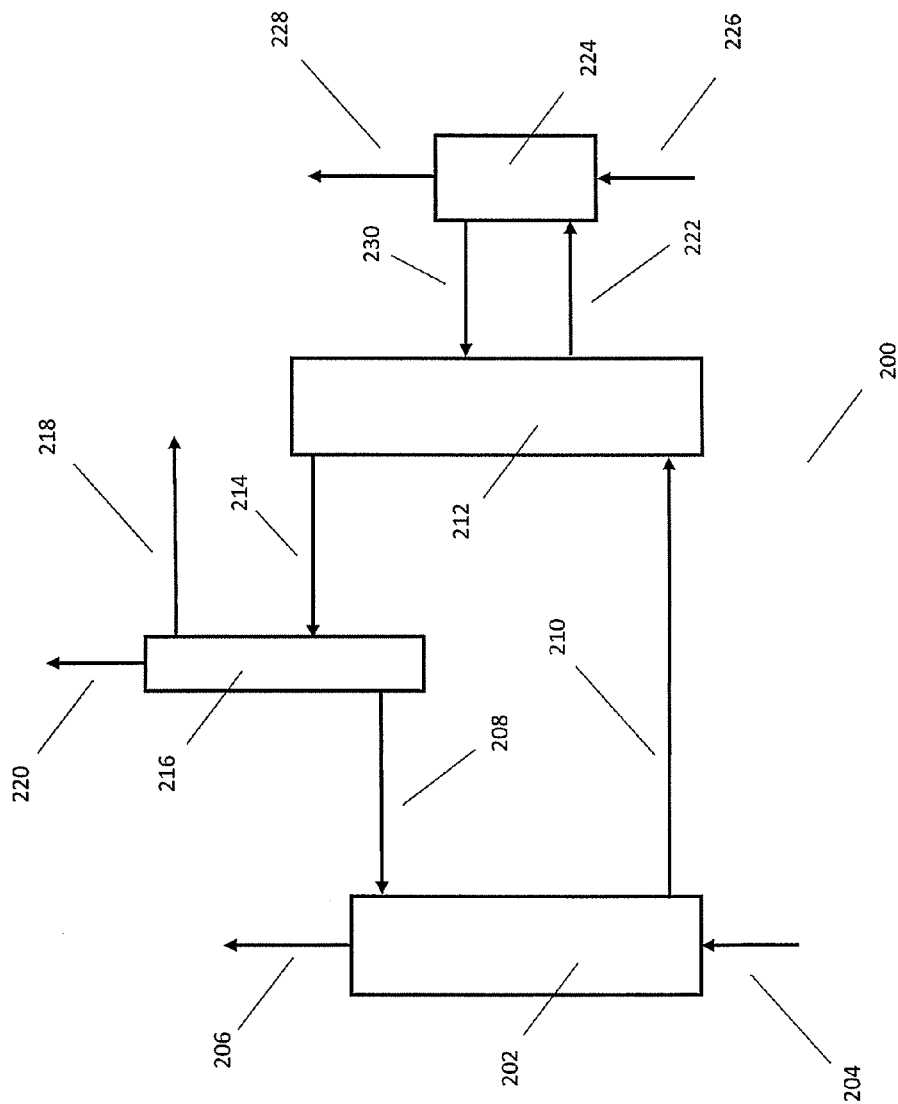
FIG. 2 is a schematic depiction of an apparatus that can be used in the processes of this invention in which water-insoluble liquid is passed into an absorber for contact with substrate, and once ladened with substrate, is passed into a bioreactor assembly for bioconversion of the substrate.

With reference to FIG. 2, apparatus 200 depicts the use of an absorption column to recover substrate from a gaseous stream. As shown, absorption column 202 receives a gaseous stream containing hydrogen, carbon monoxide and carbon dioxide from line 204. Absorption column 202 provides for countercurrent contact with water-insoluble liquid, which for purposes of discussion is toluene. Absorbed gases exit absorption column 202 via line 206. The water-insoluble liquid is provided to absorption column 202 via line 208. The water-insoluble liquid containing substrate, i.e., hydrogen, carbon monoxide and carbon dioxide, exits absorption column 202 via line 210, and is passed to bioreactor assembly 212.

Bioreactor assembly 212 contains ME biocatalyst contained therein microorganisms adapted to convert syngas to ethanol. Water-insoluble liquid laden with ethanol is continuously withdrawn from bioreactor assembly 212 via line 214 and passed to distillation column 216. Distillation column 216 provides an ethanol offtake via line 218. Lights, such as methane and nitrogen as well as any unreacted syngas exits distillation column 216 via line 220. A bottoms fraction containing toluene is withdrawn from distillation column 216 the line 208 and returned to absorption column 202.

As shown, ME biocatalyst is withdrawn from bioreactor assembly 212 via line 222 and is passed to rehydration tank 224. As with FIG. 1, an aqueous medium containing nutrients for the microorganisms is supplied to rehydration tank 224 by line 226. An aqueous stream is withdrawn from rehydration tank 224 via line 228. The biocatalyst, having been rehydrated, is passed via line 230 to bioreactor assembly 212.

While not particularly shown in FIG. 2, it is to be understood that the various unit operations described in connection with FIG. 1 can be used to assure that a separate aqueous phase does not get formed external to the biocatalyst.

In an alternative deployment, the apparatus of FIG. 2 can be used to remove nitrogen oxides from flue gases. In such situations, bioreactor assembly 212 contains denitrification microorganisms, and a nitrogen-containing gas may directly be evolved from the bioreactor assembly without the need for distillation column 216. Also, the aqueous medium provided to rehydration tank 224 will need to contain a carbon source for the microorganisms to retain their viability.

EXAMPLES

Example 1

A biocatalyst is prepared for the bioconversion of sugar to ethanol. The following procedure is used. The microorganisms (*Saccharomyces cerevisiae* ATCC® 9763™) for the biocatalyst are grown under suitable planktonic conditions in an aqueous medium for the microorganisms including the presence of nutrients and micronutrients. This medium is referred to herein as the "Culture Medium". The microorganisms used are as available and thus may be either substantially pure strains or mixed cultures. The cell density in the Culture Medium is determined by optical density. If too thick, the cell density is determined through filtration of solids and determining the mass of solids per unit volume. If the cell density of the Culture Medium is below that sought to make the biocatalyst, the Culture Medium is centrifuged or filtered to provide a denser, cell-containing fraction. A separately prepared aqueous solution of solubilized precursor is made (referred to herein as the "Polymer Solution"). The Polymer Solution contains 15.0 wt. percent of polyvinyl alcohol available as Mowial® 28-99 from Kuraray Co., Ltd. having a degree of hydrolysis of 99.0-99.8 mol percent and a molecular weight of 145,000; 3.5 wt. percent of sodium alginate available as Nalgin™ MV-120 from Ingredient Solutions, Inc. The Polymer Solution is mixed with a mechanical stirrer to assure uniform dispersion of the components in the aqueous medium. Where necessary to solubilize the precursor, the Polymer Solution can be heated as appropriate. In some instances, a micronutrient solution is also added to the Polymer Solution.

Aliquots of each of the Culture Medium (or dense phase from centrifugation) and Polymer Solution are admixed under mechanical stirring at about 30° C. to for a Precursor Solution. About 70 volume parts of Polymer Solution are used per 100 parts of Precursor Solution. The microorganism density is about 310 grams per liter.

The Precursor Solution is then extruded through a perforated plate having orifices of about 0.75 millimeter in diameter to form droplets of about 3 millimeters in diameter. The droplets fall into a gently stirred coagulating bath of an aqueous boric acid solution having a pH of about 5. The biocatalyst is recovered from the coagulating bath and washed with distilled water. The biocatalyst, after washing, is placed in a liquid medium containing micronutrients and the substrate under suitable metabolic conditions for the microorganisms.

The biocatalyst is used to bioconvert glucose contained in an aqueous medium to ethanol. The aqueous medium contains a nutrient package. The aqueous medium is then drained from the biocatalyst and the biocatalyst is at the point of incipient wetness.

Example 2

About 100 milliliters of dodecanol are placed in a glass bioreactor and heated to about 32° C. Then about 5 grams of glucose (powder) are added to the dodecanol to provide an initial glucose concentration of about 50 grams per liter. Most of the glucose remains undissolved, and the liquid is gray and cloudy. About 20 grams of the biocatalyst of Example 1 are added. No nutrients are added. The bioreactor is sealed and placed in an incubator shaker with shaking at medium speed. The bioreactor is provided with a tube to permit carbon dioxide to escape and the tube is directed to water in a trap to enable observation of carbon dioxide evolution.

After about 3 hours the liquid in the bioreactor becomes clear and the evolution of carbon dioxide is evident from the bubbles passing through the trap. After about 72 hours, the bioreactor is removed from the incubator, and a small aliquot sample of the liquid is analyzed for glucose content, which is determined to be present in an amount of less than about 1 gram per liter. A small aliquot sample of the liquid is analyzed by gas chromatography and is found to contain about 25 grams per liter of ethanol. No aqueous phase is observed in the dodecanol and the biocatalyst appears to retain its size, both evidencing that the biocatalyst maintains the aqueous medium in it interior.

It is believed that the dissipation of the cloudy solution of glucose in the dodecanol is due to the generation of ethanol during the initial three hour period. Hence, when about 5 grams of glucose (powder) are added to the bioreactor after taking samples for the analyses, a substantially clear solution is obtained. In a further confirmation, about 5 grams of the glucose powder are added to a mixture of 100 milliliters of dodecanol and 2.5 milliliters of anhydrous ethanol. A clear solution is observed.

The biocatalyst used in this example retains its ability to bioconvert sugars to ethanol.

APPENDIX A

Representative microorganisms include, without limitation, *Acetobacter* sp., *Acetobacter aceti*, *Achromnobacter*, *Acidiphilium*, *Acidovorax delafieldi* P4-1, *Acinetobacter* sp. (*A. calcoaceticus*), *Actinomnadura*, *Actinoplanes*, *Actinomycetes*, *Aeropyrum pernix*, *Agrobacterium* sp., *Alcaligenes* sp. (*A. dentrificans*), *Alloiococcus otitis*, *Ancylobacter aquaticus*, *Ananas comosus* (M), *Arthrobacter* sp. *Arthrobacter sulfurous*, *Arthrobacter* sp. (*A. protophormiae*), *Aspergillus* sp., *Aspergillus niger*, *Aspergillus oryze*, *Aspergillus melleus*, *Aspergillus pulverulentus*, *Aspergillus saitoi*, *Aspergillus sojea*, *Aspergillus usamii*, *Bacillus alcalophilus*, *Bacillus amyloliquefaciens*, *Bacillus brevis*, *Bacillus circulans*, *Bacillus clausii*, *Bacillus cereus*, *Bacillus lentus*, *Bacillus licheniformis*, *Bacillus macerans*, *Bacillus stearothermophilus*, *Bacillus subtilis*, *Beijerinckia* sp., *Bifidobacterium*, *Brevibacterium* sp. HL4, *Breltanomyces* sp., *Brevibacillus brevis*, *Burkholderia cepacia*, *Campylobacter jejuni*. *Candida* sp., *Candida cylindracea*, *Candida rugosa*, *Carboxydothermus* (*Carboxydothermus hydrogenoformans*), *Carica papaya* (L), *Cellulosimicrobium*, *Cephalosporium*, *Chaetomium erraticum*, *Chaetomium gracile*, *Chlorella* sp. *Citrobacter*, *Clostridium* sp., *Clostridium butvricum*, *Clostridium acetobutylicum*, *Clostridium kluyveri*, *Clostridium carboxidivorans*, *Clostridium thermocellum*, *Cornynebacterium* sp. strain m15, *Corynebacterium* (*glutamicum*), *Corynebacterium efficiens*, *Deinococcus radiophilus*, *Dekkera*. *Dekkera bruxellensis*, *Escherichia coli*, *Enterobacter* sp., *Enterococcus*, *Enterococcus faecium*, *Enterococcus gallinarium*, *Enterococcus faecalis*, *Erwinia* sp. *Erwinia chrysanthemi*, *Gliconobacter*, *Gluconacetobacter* sp., *Hansenula* sp., *Haloarcula*, *Humicola insolens*, *Humicola nsolens*. *Kitasatospora setae*, *Klebsiella* sp., *Klebsiella oxytoca*, *Klebsiella pneumonia*, *Kluyveromyces* sp., *Kluyveromyces fragilis*, *Kluyveromyces lactis*, *Kocuria*, *Lactlactis*, *Lactobacillus* sp., *Lactobacillus fermentum*, *Lactobacillus sake*, *Lactococcus*, *Lactococcus lactis*, *Leuconostoc*, *Methylosinus trichosporum* OB3b, *Methylosporovibrio methanica* 812, *Methanothrix* sp. *Methanosarcina* sp., *Methanomonas* sp., *Methylocystis*, *Methanospirilium*, *Methanolobus siciliae*, *Methanogenium organophilum*, *Methanobacerium* sp., *Methanobacterium bryantii*, *Methanococcus* sp., *Methanomicrobium* sp., *Methanoplanus* sp., *Methanosphaera* sp., *Methanolobus* sp., *Methanoculleus* sp., *Methanosaeta* sp., *Methanopyrus* sp., *Methanocorpusculum* sp., *Methanosarcina*, *Methylococcus* sp., *Methylomonas* sp. *Methylosinus* sp. *Microbacterium imperiale*, *Micrococcus* sp., *Micrococcus lysodeikticus*, *Microlunalus*, *Moorella* (e.g., *Moorella* (*Clostridium*) *thermoacetica*), *Moraxella* sp. (strain B), *Morganella*, *Mucorjavanicus*, *Mvcobacterium* sp. strain GP1, *Myrothecium*, *Neptunomonas naphthovorans*, *Nitrobacter*, *Nitrosomonas* (*Nitrosomonas europea*), *Nitzchia* sp., *Nocardia* sp., *Pachysolen* sp., *Pantoea*, *Papaya carica*, *Pediococcus* sp., *Pediococcus halophilus*, *Penicillium*, *Penicillium camemberti*, *Penicillium citrinum*, *Penicillium emersonii*, *Penicillium roqueforti*, *Penicillum lilactinum*, *Penicillum multicolor*, *Phanerochaete chrysoporium*, *Pichia* sp., *Pichia stipitis*, *Paracoccus pantotrophus*, *Pleurotus ostreatus*, *Propionibacterium* sp., *Proteus*, *Pseudomonas* (*P. pavonaceae*, *Pseudomonas* ADP, *P. stutzeri*, *P. putida*, *Pseudomonas* Strain PSI, *P. cepacia* G4, *P. medocina* KR, *P. picketti* PK01, *P. vesicularis*, *P. paucimobilis*, *Pseudomonas* sp. DLC-P11, *P. mendocina*, *P. chichhori*, strain IST 103), *Pseudomonas fluorescens*, *Pseudomonas denitrificans*, *Pyrococcus*, *Pyrococcus fririosus*, *Pyrococcus horikoshii*, *Ralstonia* sp., *Rhizobium*, *Rhizomucor miehei*, *Rhizomucor pusillus* Lindt, *Rhizopus*, *Rhizopus delemar*, *Rhizopus japonicus*, *Rhizopus niveus*, *Rhizopus oryzae*, *Rhizopus oligosporus*, *Rhodococcus*, (*R. erythropolis*, *R. rhodochrous* NCIMB 13064). *Salmonella*, *Saccharomyces* sp., *Saccharomyces cerevisiae*, *Schizochytriu* sp., *Sclerotina libertina*, *Serratia* sp., *Shigella*, *Sphingobacterium multivorum*, *Sphingobium* (*Sphingbium chlorophenolicum*), *Sphingomonas* (*S. yanoikuvae*, *S.* sp. RW1), *Streptococcus*, *Streptococcus thermophilus* Y-1, *Streptomyces*, *Streptomyces griseus*, *Streptomyces lividans*, *Streptomyces murinus*, *Streptomyces rubiginosus*, *Streptomyces violaceoruber*, *Streptoverticillium mobaraense*, *Synechococcus* sp., *Synechocystis* sp., *Tetragenococcus*, *Thermus*, *Thiosphaera pantotropha*, *Trametes*, *Trametes versicolor*, *Trichoderma*, *Trichoderma longibrachiatum*, *Trichoderma reesei*, *Trichoderma viride*, *Trichosporon* sp., *Trichosporon penicillatum*, *Vibrio alginolyticus*, *Xanthomonas*, *Xanthobacter* sp. (*X. autotrophicus* GJ 10, *X. flavus*), yeast, *Yarrow lipolytica*, *Zygosaccharomyces rouxii*, *Zvmomonas* sp. *Zymomonus mobilis*, *Geobacter sulfurreducens*, *Geobacter lovleyi*, *Geobacter metallireducens*, *Bacteroides succinogens*, *Butyrivibrio fibrisolvens*, *Clostridium cellobioparum*, *Ruminococcus albus*, *Ruminococcus flavefaciens*, *Eubacterium cellulosolvens*, *Clostridium cellulosolvens*, *Clostridium cellulovorans*, *Clostridium thermocellum*, *Bacteroides cellulosolvens*, and *Acetivibrio cellulolyticus* *Gliricidia* sp., *Albizia* sp., or *Parthenium* sp. *Cupriavidus basilensis*, *Cupriavidus campinensis*, *Cupriavidus gilardi*, *Cupriavidus laharsis*, *Cupriavidus metallidurans*, *Cupriavidus oxalaticus*, *Cupriavidus pauculus*, *Cupriavidus pinatubonensis*, *Cupriavidus respiraculi*, *Cupriavidus taiwanensis*, *Oligotropha carboxidovorans*, *Thiobacillus* sp., *Thiobacillus denitrificans*, *Thiobacillus thioxidans*, *Thiobacillus ferrooxidans*, *Thiobacillus concretivorus*, *Acidithiobacillus albertensis*, *Acidithiobacillus caldus*, *Acidithiobacillus cuprithermicus*, *Rhodopseudomonas*, *Rhodopseudomonas palustris*, *Rhodobacter sphaeroides*, *Rhodopseudomonas capsulate*, *Rhodopseudomonas acidophila*, *Rhodopseudomonas viridis*, *Desulfotomaculum*, *Desulfotomaculum acetoxidans*, *Desulfotomaculum kuznetsovii*, *Desulfotomaculum nigrificans*, *Desulfotomaculum reducens*, *Desulfotomaculum carboxydivorans*, *Methanosarcina barkeri*, *Methanosarcina acetivorans*, *Moorella thermoacetica*, *Carboxydothermus hydrogenoformans*, *Rhodospirillum rubrum*, *Acetobacterium woodii*, *Butyribacterium methylotrophicum*, *Clostridium autoethanogenum*, *Clostridiumn ljungdahlii*, *Eubacterium limosum*, *Oxobacter pfennigii*, *Peptostreptococcus productus*, *Rhodopseudomonas palustris* P4, *Rubrivivax gelatinosus*, *Citrobacter* sp Y19, *Methanosarcina acetivorans* C2A, *Methanosarcina barkeri*, *Desulfosporosinus orientis*, *Desulfovibrio desulfuricans*, *Desulfovibrio vulgaris*, *Moorella* thermoautotrophica, Carboxydibrachium pacificus, Carboxydocella thermoautotrophica, Thermincola carboxydiphila, Thermolithobacter carboxydivorans, Thermosinus carboxydivorans, Methanothermobacter thermoautotrophicus, Desulfotomaczdum carboxydivorans, Desulfotomaculum kusnetsovii, Desulfotomaculum nigrificans, Desulfotomaculum thermobenzoicum subsp. thermosyntrophicumn, Syntrophobacter fumaroxidans, Clostridium acidurici, Desulfovibrio africanus, C. pasteurianum, C. pasteurianum DSM 525. Paenibacillus polymyxa, Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botrvococcus, Botryosphaerella, Brachiomonas, Brachysira, Brachytrichia, Brebissonia, Bulbochaete, Bunilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamnaesiphon, Chara, Characiochloris, Characiopsis, Characium, Charales, Chilomonas, Chlainomonas, Chlanydoblepharis, Chlamydocapsa, Chlamydomnonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterlum, Coccomyxa, Cocconeis, Coelastrella, Coelastrunm, Coelosphaerium, Coenochloris, Coenococcus, Coenocvstis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca. Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatomna, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifllum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothri, Ellerbeckia, Encyonema, Enteromorpha, Entocladia, Entomoneis, Entophvsalis, Epichrysis, Epipyxis, Epithemia, Eremosphaera, Euastropsis, Euastrum, Eucapsis, Eucocconeis, Eudorina, Euglena, Euglenophyla, Eunotia, Eusligmatophyla, Eutreplia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocysis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Ilammatoidea, Hannaea, Hantzschia, Hapalosiphon, Haplotaenium, Haptophyta, Haslea, Hemidinium, Hemitoma, Heribaudiella, Hleleromastix, Ileterothrix, Hibberdia, Hildenbrandia, Hillea, Holopedium, Homoeothrix, Hormanthonema, Hormotila, Hyalobrachion, Hyalocardiumn, Hvalodiscus, Hyalogonium, Hvalotheca, Hydrianum, Hydrococcus, Hydrocoleum, Hydrocoryne, Hydrodictyon, Hydrosera, Hydrurus, Hvella, Hymenomonas, Isthmochloron, Johannesbaptislia, Juranyiella, Karayevia, Kathablepharis, Katodinium, Kephyrion, Keralococcus, Kirchneriella, Klebsormidiunm, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micraclinium, Micrasterias, Microchaete, Microcoleus, Microcystis, Microglena, Micromonas. Microspora, Microthamnion, Mischococcus, Monochrysis, Monodus, Monomastix, Monoraphidium, Monostroma, Mougeotia, Mougeotiopsis, Mvochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaelophora, Onychonema, Oocardium, Oocystis, Opephora, Ophiocytium, Orthoseira, Oscillatoria, Oxvneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Pryinesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocyslis, Pseudostaurastrunm, Pseudostaurosira, Pseudotetrastrum, Pteromonas, Punciastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Rowa, Scenedesmus, Scherffelia, Schizochlamydella, Schizochlamys, Schizomeris, Schizothrix, Schroederia, Scolioneis, Scotiella, Scotiellopsis, Scoutfieldia, Scytonema, Selenastrum, Selenochloris, Sellaphora, Semiorbis, Siderocelis, Diderocysiopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondvylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Siichogloea, Stigeoclonium, Stigonema, Stipitococcus, Stokesiella, Strombonmonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracvclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Weslella, Woloszvnskia, Xanthidium, Xanthophyta, Xenococcus, Zygnema, Zygnemopsis, Zygonium, Chlorollexus, Chloronema, Oscillochloris, Heliothrix, Herpetosiphon, Roseiflexus, Thermomicrobium, Chlorobium, Clathrochloris, Prosthecochloris, Allochromatium, Chromatium, Halochromatium, Isochromatium, Marichromatium, Rhodovulum, Thermochromatium, Thiocapsa, Thiorhodococcus, Thiocystis, Phaeospirillum. Rhodobaca, Rhodobacter, Rhodomicrobium, Rhodopila, Rhodopseudomonas, Rhodothalassium, Rhodospirillum, ovibrio, Roseospira, Nitrobacteraceae sp., Nitrobacter sp., Nitrospina sp., Nitrococcus sp., Nitrospira sp., Nitrosomonas sp., Nitrosococcus sp., Nitrosospira sp., Nitrosolobus sp., Nitrosovibrio sp., Thiovulum sp., Thiobacillus sp., Thiomicrospira sp., Thiosphaera sp., Thermothrix sp., Hydrogenobacter sp., Siderococcus sp., Aquaspirillum sp. Methanobacterium sp., Methanobrevibacter sp., Methanothermus sp., Methanococcus sp., Methanomicrobium sp., Methanospirillum sp., Methanogenium sp., Methanosarcina sp., Methanolobus sp. Methanothrix sp., Methanococcoides sp., Methanoplanus sp., Thermoproteus sp., Pyrodictium sp., Sulfolobus sp., Acidianus sp., Bacillus subtilis, Saccharomyces cerevisiae, Streptomyces sp., Ralstonia sp., Rhodococcus sp., Corynebacieria sp., Brevibacteria sp., Mycobacteria sp., oleaginous yeast, Arabidopsis thaliana, Panicum virgatum, Miscanthus giganteus, Zea mays (plants), Botryococcus braunii, Chlamydomonas reinhardtii and Dunaliela salina (algae), Synechococcus sp PCC 7002, Synechococcus sp. PCC 7942, Synechocystis sp. PCC 6803, Thermosynechococcus elongatus BP-1 (cyanobacteria), Chlorobium tepidum (green sulfur bacteria), Chloroflexus auranticusl, Chromatium tepidum and Chromatium vinosum (purple sulfur bacteria), Rhodospirillum rubrum, Rhodobacter capsulatus, and Rhodopseudomonas palusris (purple non-sulfur bacteria).

It is claimed:

1. A process for the bioconversion of substrate to bioproduct comprising:
   a. providing in a bioreactor assembly a water-insoluble liquid containing said substrate;
   b. contacting said water-insoluble liquid in said bioreactor assembly with an internally hydrated biocatalyst under metabolic conditions for a time sufficient to bioconvert at least a portion of said substrate to said bioproduct wherein said water-insoluble liquid is capable of receiving said bioproduct from the interior of said biocatalyst to provide a bioproduct-containing liquor, said contacting being substantially absent an aqueous phase external to said biocatalyst, wherein said biocatalyst comprises:
      i. a solid structure of hydrated hydrophilic polymer defining an interior structure having a plurality of interconnected major cavities having a smallest dimension of between about 5 and 100 microns and a Hydration Expansion Volume (HEV), which is calculated in volume percent of about 1000 or more and
      ii. a population of microorganisms capable of converting said substrate to said bioproduct, said population of microorganisms being substantially irreversibly retained in the interior of the solid structure, said population of microorganisms being in a concentration of about 60 grams per liter or more based upon the volume defined by the exterior of the solid structure when fully hydrated wherein the microorganisms maintain a their population substantially stable; and
   c. separating said bioproduct from said bioproduct-containing liquor.

2. The process of claim 1 wherein substrate is continuously or intermittently fed to the bioreactor assembly.

3. The process of claim 1, wherein at least a portion of the bioproduct-containing liquor is withdrawn from the bioreactor assembly and bioproduct is separated from the withdrawn bioproduct-containing liquor.

4. The process of claim 1, wherein the bioproduct comprises oxygenated organic compound.

5. The process of claim 4, wherein the oxygenated organic compound comprises alcohol that forms an azeotrope with water, and the separation is by distillation in the absence of formation of the azeotrope.

6. The process of claim 5 wherein the alcohol comprises 1 to 4 carbon atoms.

7. The process of claim 4, wherein the oxygenated organic compound comprises at least one of succinic add or ester thereof, lactic add or ester thereof, or diol of 2 to 6 carbons.

8. The process of claim 1, wherein the substrate comprises a normally gaseous moiety.

9. The process of claim 8, wherein the normally gaseous component is at least one of oxygen; hydrocarbon of 1 to 4 carbons; chloromethane; chlorodifluoromethane; difluoromethane; dichlorodifluoromethane; 1,1,1,2-tetrafluoroethane; 2-chloro-1,1,1,2-tetrafluoroethane; pentafluoroethane; chloropentafluoroethane; nitric oxide; nitrous oxide; nitrogen dioxide; carbon monoxide; carbon dioxide; hydrogen; hydrogen sulfide; sulfur dioxide; and ammonia.

10. The process of claim 1, wherein
   a. at least a portion of the bioproduct-containing liquor is withdrawn from the bioreactor assembly and bioproduct is separated from the withdrawn bioproduct-containing liquor to provide a regenerated liquor,
   b. substrate is supplied to at least a portion of the regenerated liquor to provide a feed liquor, and c. the feed liquor is introduced into the bioreactor assembly as at least a portion of the water-insoluble liquid containing said substrate.

11. The process of claim 1, further comprising:

continuously or intermittently ceasing contact between at least a portion of the biocatalyst and the water-insoluble liquid;

b. contacting the biocatalyst with an aqueous medium comprising nutrients for said microorganism to provide an internally rehydrated biocatalyst;

C. removing excess aqueous medium from said internally rehydrated biocatalyst; and d. contacting the internally rehydrated biocatalyst with the water-immiscible liquid in said bioreactor assembly.

12. The process of claim 1, wherein the bioconversion is a photosynthetic conversion.

13. The process of claim 1, wherein the bioconversion is anabolic.

14. The process of claim 1, wherein the bioconversion is catabolic.

* * * * *